US008238568B2

(12) United States Patent
Miseki et al.

(10) Patent No.: US 8,238,568 B2
(45) Date of Patent: Aug. 7, 2012

(54) ACOUSTIC SIGNAL COMPENSATOR AND ACOUSTIC SIGNAL COMPENSATION METHOD

(75) Inventors: Kimio Miseki, Tokyo (JP); Norikatsu Chiba, Tokyo (JP); Yasuhiro Kanishima, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 12/888,321

(22) Filed: Sep. 22, 2010

(65) Prior Publication Data

US 2011/0170700 A1 Jul. 14, 2011

(30) Foreign Application Priority Data

Jan. 13, 2010 (JP) ................................ 2010-005303

(51) Int. Cl.
*H03B 29/00* (2006.01)
*A61F 11/06* (2006.01)
*G10K 11/16* (2006.01)

(52) U.S. Cl. ..................................... 381/71.6; 381/94.2

(58) Field of Classification Search ................. 381/71.1, 381/71.14, 74, 23.1, 370, 317, 320, 94.1, 381/94.2; 181/135, 130
See application file for complete search history.

(56) References Cited

U.S. PATENT DOCUMENTS 4,677,679 A * 6/1987 Killion ........................... 381/74
2005/0271367 A1* 12/2005 Lee et al. ........................ 386/96
2009/0208027 A1 8/2009 Fukuda et al.
2009/0296949 A1 12/2009 Iwata et al.
2010/0142726 A1 6/2010 Donaldson
2010/0177910 A1* 7/2010 Watanabe ................... 381/94.1

FOREIGN PATENT DOCUMENTS

JP 9-187093 7/1997
JP 2000-092589 3/2000
JP 2003-304599 10/2003
JP 2008-177798 7/2008
JP 2009-516409 4/2009
JP 2009-194769 8/2009
JP 2009-288555 12/2009

OTHER PUBLICATIONS

Japanese Patent Application No. 2010-005303; Notice of Reasons for Rejection; Mailed Dec. 7, 2010 (English translation).
"A Rating System of Headphones and Earphones Using Transfer Function of External Auditory Canal", Adachi Dai (and another), Report of the Institute of Electronics, Information, and Communications Engineers (IEICE), EA, applied acoustics, Japan, Oct. 22, 2004, vol. 104, pp. 43 to 48.

* cited by examiner

*Primary Examiner* — Vivian Chin
*Assistant Examiner* — Con P Tran
(74) *Attorney, Agent, or Firm* — Blakely, Sokoloff, Taylor & Zafman LLP

(57) ABSTRACT

According to one embodiment, an acoustic signal compensator includes an acoustic signal receiving module, a compensator, and an output module. The acoustic signal receiving module receives an acoustic signal. The compensator performs compensation on the acoustic signal, as compensation of acoustic characteristics of an ear including an ear canal having a first-order resonance characteristic and a second-order resonance characteristic, to suppress a first-order frequency of ear resonance and a second-order frequency lower than double of the first-order frequency. The output module outputs the acoustic signal compensated by the compensator.

11 Claims, 16 Drawing Sheets

ACOUSTIC SIGNAL COMPENSATOR AND ACOUSTIC SIGNAL COMPENSATION METHOD

CROSS-REFERENCE TO RELATED APPLICATIONS

This application is based upon and claims the benefit of priority from Japanese Patent Application No. 2010-005303, filed Jan. 13, 2010, the entire contents of which are incorporated herein by reference.

FIELD

Embodiments described herein relate generally to an acoustic signal compensator and an acoustic signal compensation method.

BACKGROUND

When a user listens to music with earphones or headphones, the sound resonates in the space formed by his/her ears and the earphones or the headphones. The resonance phenomenon causes the user to hear an unnatural sound. To avoid such an unnatural sound, there has been proposed a system aimed at canceling the resonance phenomenon in the space formed by the ears and the earphones or the headphones.

For example, Japanese Patent Application Publication (KOKAI) No. 2009-194769 discloses a conventional technology for cancelling a peak of a resonant frequency detected by specific earphones for measurement purposes provided with a microphone. According to the conventional technology, a sound source signal is output from the earphones. While the earphones are placed in the ear canal, the microphone picks up sound to obtain the frequency characteristics of the acoustic signals. The resonant frequency of the ear canal is detected from the frequency characteristics to reduce the resonant frequency.

Japanese Patent Application Publication (KOKAI) No. H9-187093 discloses a conventional technology for determining a specific variable to suppress the resonant frequency. According to the conventional technology, since music listening in high volume may damage hearing ability, the sound level is reduced to around the resonant frequency of the human ear.

The latter conventional technology does not identify the relation between earphones and ears. Although it is described how to reduce the sound level for only a single resonance, there is not always only one resonant frequency band. It is often the case that a plurality of orders of resonant frequency bands are present. These resonant frequency bands to be reduced differ depending on the environment such as individuals or earphones.

With the above conventional technologies, the earphones need to have a specific structure that the microphone is integrated with the earphone player, and the resonant frequency has to be measured by picking up sounds using the microphone. This means that the conventional technologies cannot be realized by commonly used earphones. The microphone of the specific earphones measures the resonant frequency in a space formed by the specific earphones and ears, and the resonant frequency is different from that when the user uses common earphones. That is, the conventional technologies are not applicable to common earphones and cannot reduce the resonant frequency that varies according to a combination of user's ears and earphones. Therefore, sound cannot be reproduced in high quality.

BRIEF DESCRIPTION OF THE SEVERAL VIEWS OF THE DRAWINGS

A general architecture that implements the various features of the invention will now be described with reference to the drawings. The drawings and the associated descriptions are provided to illustrate embodiments of the invention and not to limit the scope of the invention.

DETAILED DESCRIPTION

Various embodiments will be described hereinafter with reference to the accompanying drawings. In general, according to one embodiment, an acoustic signal compensator comprises an acoustic signal receiving module, a compensator, and an output module. The acoustic signal receiving module is configured to receive an acoustic signal. The compensator is configured to perform compensation on the acoustic signal, as compensation of acoustic characteristics of an ear including an ear canal having a first-order resonance characteristic and a second-order resonance characteristic, to suppress a first-order frequency of ear resonance and a second-order frequency lower than the double of the first-order frequency. The output module is configured to output the acoustic signal compensated by the compensator.

According to another embodiment, an acoustic signal compensator comprises an acoustic signal receiving module, a compensator, and an output module. The acoustic signal receiving module is configured to receive an acoustic signal. The compensator is configured to perform compensation on the acoustic signal, as compensation of acoustic characteristics of an ear including an ear canal having a first-order resonance characteristic and an Nth-order resonance characteristic (N: an integer 2 or more) to suppress a first-order frequency of ear resonance and an Nth-order frequency lower than a value obtained by multiplying the first-order frequency by N and higher than a value obtained by multiplying the first-order frequency by (N−1). The output module is configured to output the acoustic signal compensated by the compensator.

According to still another embodiment, there is provided an acoustic signal compensation method applied to an acoustic signal compensator. The acoustic signal compensation method comprises: receiving an acoustic signal; performing compensation on the acoustic signal, as compensation of acoustic characteristics of an ear including an ear canal having a first-order resonance characteristic and a second-order resonance characteristic, to suppress a first-order frequency of ear resonance and a second-order frequency lower than double of the first-order frequency; and outputting the acoustic signal compensated by the compensation.

Figure 1:
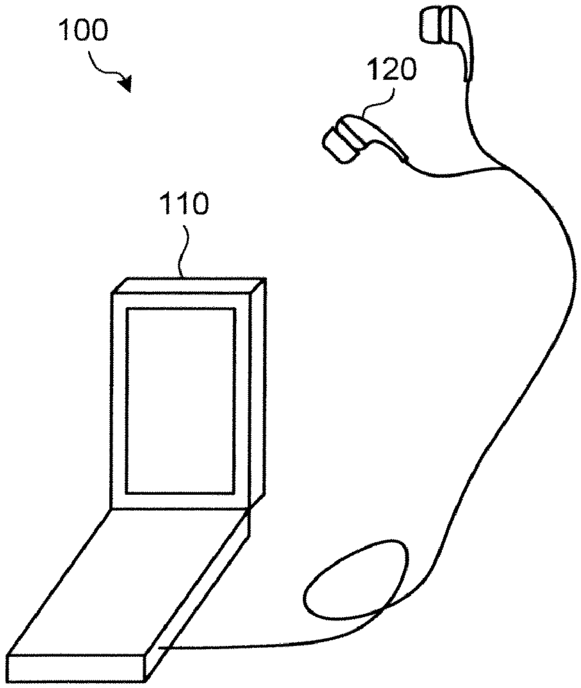
FIG. 1 is an exemplary schematic diagram of a sound processing device according to a first embodiment.

FIG. 1 is a schematic diagram of a sound processing device 100 according to a first embodiment. As illustrated in FIG. 1, the sound processing device 100 comprises a sound player 110, an acoustic signal compensator 150 built in the sound player 110, and an earphone 120. While the earphone 120 will be describes as a canal type earphone, this is by way of example and not limitation. The earphone 120 may be of any type.

When the function of the acoustic signal compensator 150 is built in the sound player 110 as illustrated in FIG. 1, the sound player 110 performs filtering on an acoustic signal using a filter coefficient derived by a pseudo anti-resonance parameter determination module 210 and outputs the acoustic signal to the earphone 120. In this case, as illustrated in FIG. 1, the acoustic signal compensator 150 does not appear outside the sound player 110. An acoustic signal is compensated inside the sound player 110 and output from the sound player 110. Therefore, an acoustic signal output module of the sound player 110 is connected to the earphone 120. The acoustic signal compensator 150 may be built in earphones or headphones. In this case also, an acoustic signal output module of the sound player 110 is connected to the earphones.

Figure 2:
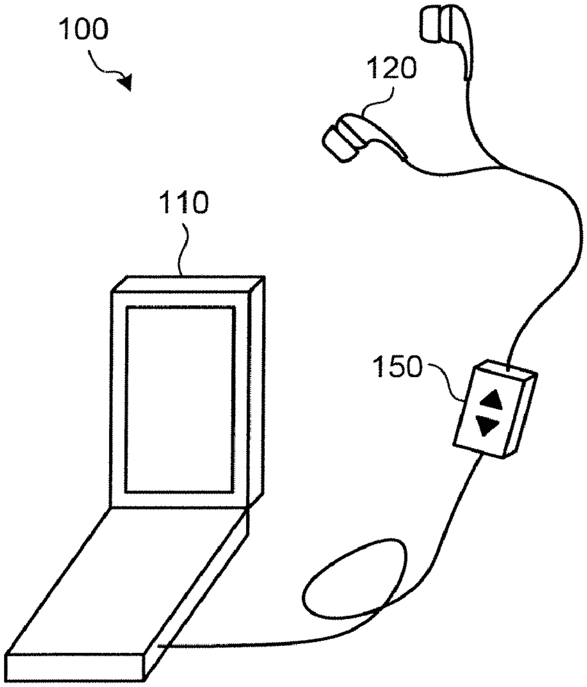
FIG. 2 is an exemplary schematic diagram of a sound processing device according to a modification of the first embodiment.

The acoustic signal compensator 150 is not so limited. For example, as illustrated in FIG. 2, the sound processing device 100 may comprise the sound player 110, the acoustic signal compensator 150 located outside the sound player 110, and the earphone 120.

Referring back to FIG. 1, the sound player 110 comprises an acoustic signal generator (not illustrated). The acoustic signal generator generates (reproduces) an acoustic signal and outputs it to the acoustic signal compensator 150 in the sound player 110. Having received the acoustic signal, the acoustic signal compensator 150 compensates the resonance characteristics of the acoustic signal, which will be described later, and outputs (reproduces) it to the ears of the user through the earphone 120.

An acoustic signal to be reproduced as a sound source is used for the compensation. Examples of acoustic signals to be reproduced include an audio signal of music or the like retrieved from memory or received from the outside. In the case of compressed data derived using audio encoding, sound encoding, lossless compression-encoding, and the like, necessary decoding may be preformed to obtain an audio waveform signal. While audio signals of two channels, i.e., L (left) and R (right) channels, are generally output, monaural signals or signals of multiple channels may be output depending on the configuration. That is, any configuration may suffice as long as compensation is performed appropriately for a number of channels necessary to reproduce signals.

Figure 3:
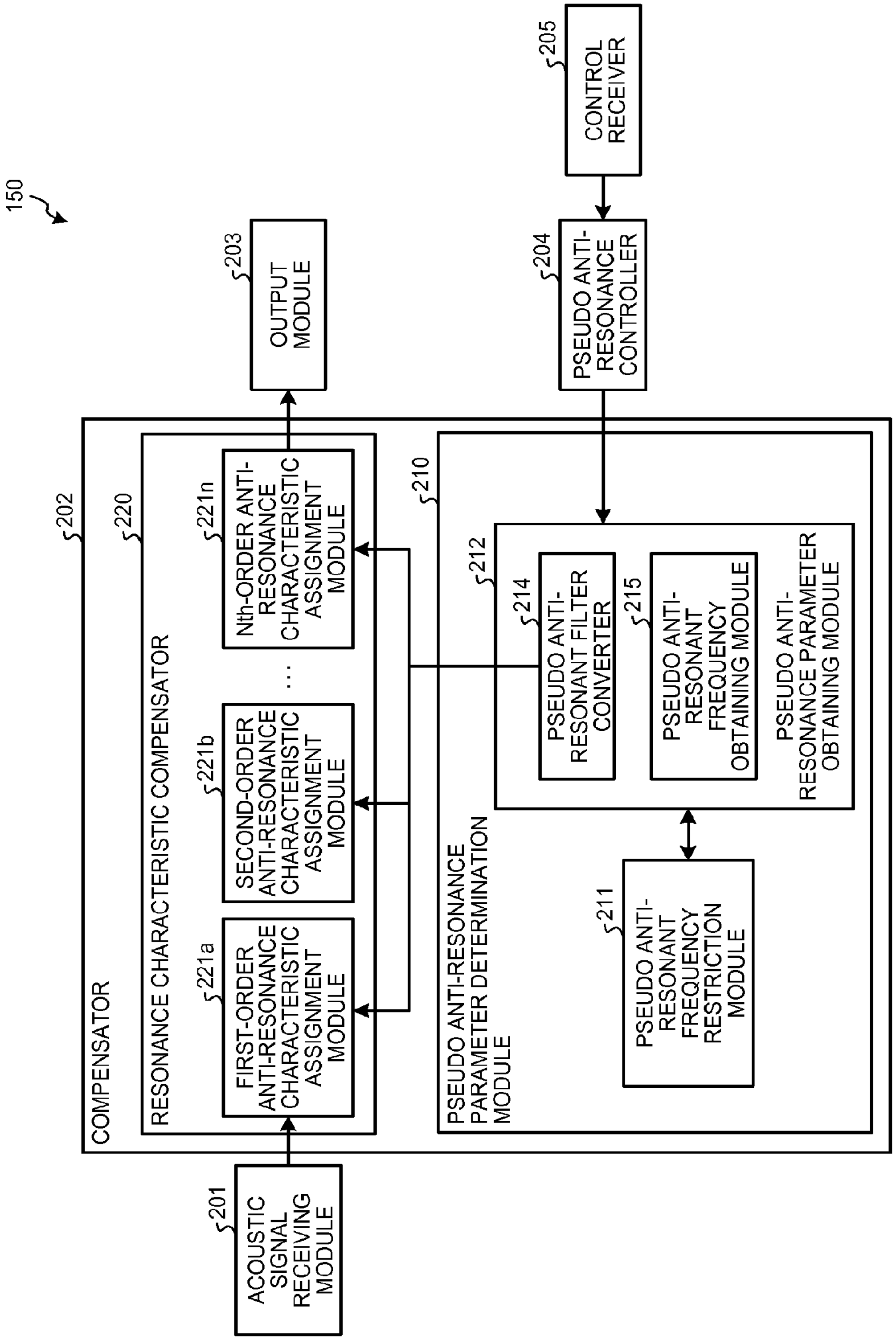
FIG. 3 is an exemplary functional block diagram of an acoustic signal compensator in the first embodiment.

The acoustic signal compensator 150 will be concretely described. FIG. 3 is a functional block diagram of the acoustic signal compensator 150 of the first embodiment. As illustrated in FIG. 3, the acoustic signal compensator 150 comprises an acoustic signal receiving module 201, a compensator 202, an output module 203, a pseudo anti-resonance controller 204, and a control receiver 205. Having received an acoustic signal from the acoustic signal receiving module 201, the acoustic signal compensator 202 compensates the acoustic signal and outputs it to the output module 203.

A description will be given of an acoustic signal to be compensated by the acoustic signal compensator 150. As described above, when the user wears earphones in his/her ears and an acoustic signal is reproduced, resonance is created in a space in each ear including the ear canal formed by the ear and the earphone.

Figure 4:
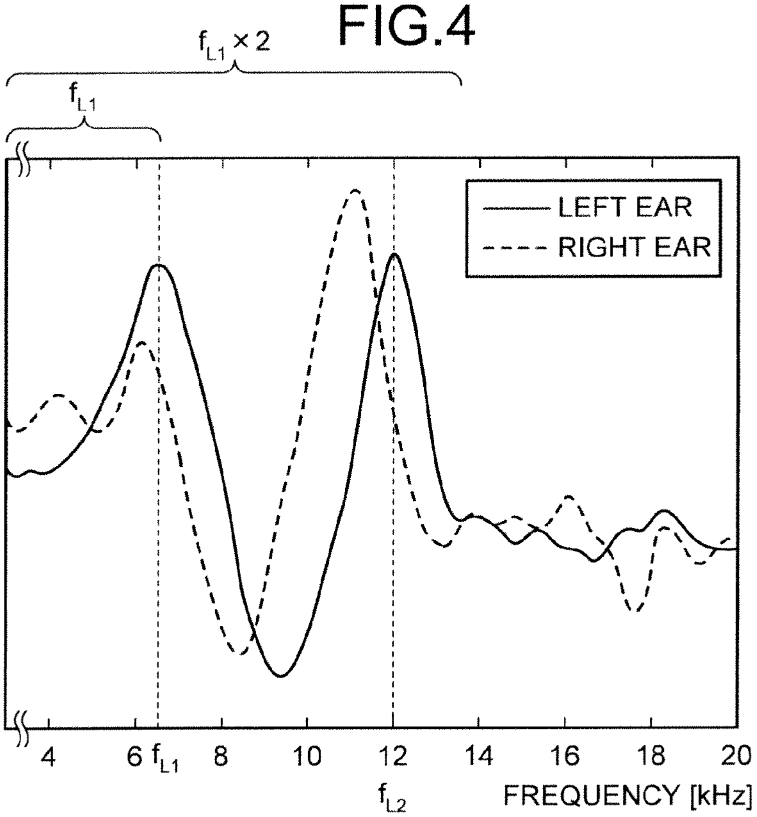
FIGS. 4 and 5 are exemplary graphs of resonance characteristics measured when earphones are placed in user's ears in the first embodiment.
Figure 5:
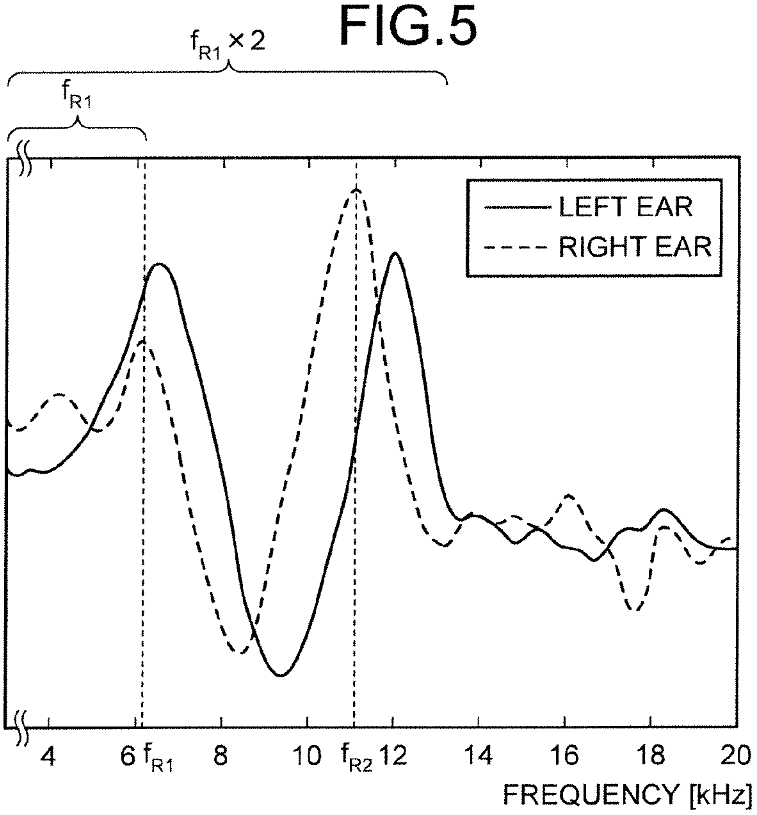

FIGS. 4 and 5 are graphs illustrating examples of measurement results of resonance obtained when earphones are placed in user's ears.

FIGS. 4 and 5 illustrates resonance characteristics measured as ear characteristics of the left and right ears of the user. In FIGS. 4 and 5, the horizontal axis represents the frequency, while the vertical axis represents the amplitude of the frequency.

As can be seen from FIGS. 4 and 5, a plurality of resonance peaks are measured as the amplitude of the frequency with respect to each of the left and right ears. The resonance peaks presumably represent the resonance of the ears. Accordingly, resonance peaks are prevented before they occur.

In the first embodiment, among a plurality of resonant frequencies the amplitudes of which create resonance peaks, a lower frequency will be referred to as "first-order resonant frequency", and resonant frequencies higher than the first-order resonant frequency will be referred to as "second-order resonant frequency", "third-order resonant frequency", and so on.

Referring to the amplitude characteristics (resonance characteristic) of the left ear indicated by the solid line in FIG. 4, $f_{L1}$ designates the first-order resonant frequency, while $f_{L2}$ designates the second-order resonant frequency. As illustrated in FIG. 4, the second-order resonant frequency $f_{L2}$ of the left ear is lower than the double of the first-order resonant frequency $f_{L1}$.

Referring to the amplitude characteristics (resonance characteristic) of the right ear indicated by the dotted line in FIG. 5, $f_{R1}$ designates the first-order resonant frequency, while $f_{R2}$ designates the second-order resonant frequency. As illustrated in FIG. 5, the second-order resonant frequency $f_{R2}$ of the right ear is lower than the double of the first-order resonant frequency $f_{L1}$. As can be seen from FIGS. 4 and 5, the resonant frequency varies depending on the ear.

That is, the shape of the inside as well as the outside of the ear varies according to the individuals, and therefore acoustic characteristics also vary according to the individuals. As a result, resonance characteristics at the time of wearing earphone also vary according to the individuals. According to the analysis of measurement results of resonance characteristics obtained from the ears of various users who are wearing earphones, ear resonance occurs mainly at a frequency higher than 5 kHz. Further, as described above, the resonance is not only the first-order resonance, but also includes the second-order and higher resonances. By preventing the second-order and higher resonances as well as the first-order resonance, acoustic signals can be reproduced in high quality for the ears of the user wearing earphones.

As can be seen from FIGS. 4 and 5 illustrating the relation between the first-order resonant frequency and the second-order resonant frequency, as described above, the second-order resonant frequency is lower than the double of the first-order resonant frequency. The above measurement data obtained from various users proves that such a relation is not specific for only the particular user, but reflects the general tendency. This may be probably because the characteristics of a closed space formed by the ear canal and an earphone inserted in the ear canal cannot be represented by the resonance of a simple closed tube.

Figure 6:
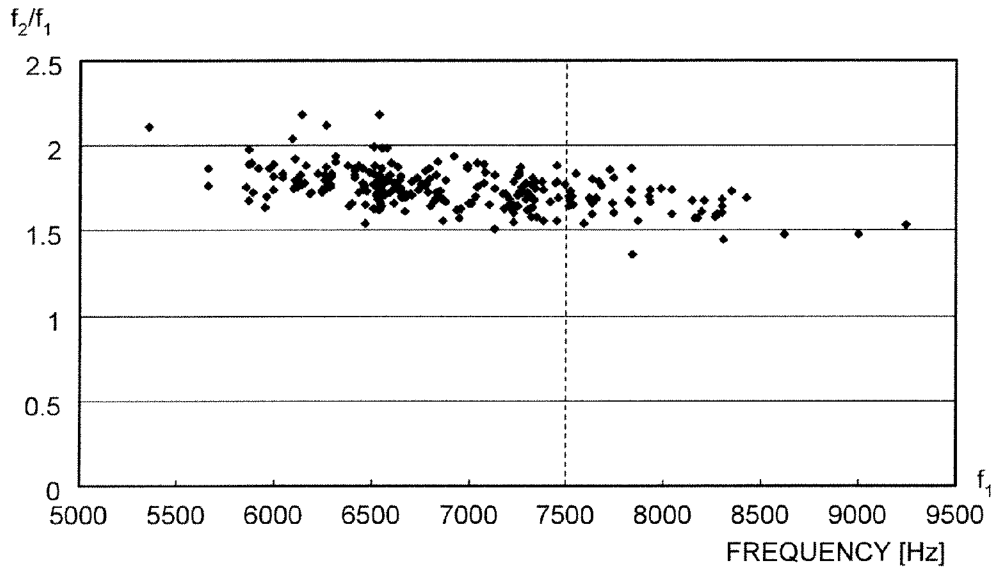
FIG. 6 is an exemplary distribution chart illustrating the ratio of second-order resonant frequencies and first-order resonant frequencies as detection results obtained from the ears of users wearing earphones in the first embodiment.

FIG. 6 is a graph plotting the relation indicating the ratio of the second-order resonant frequency and the first-order resonant frequency (f2/f1) obtained from the measurement conducted extensively on the ears of various users wearing earphones. In FIG. 6, the plots indicate data of individual users, respectively.

In the example of FIG. 6, it can be found that the first-order resonant frequency f1 is in a range of about 5 kHz to 10 kHz, while the second-order resonant frequency f2 is in a range of about 9 kHz to 15 kHz. Accordingly, it is desirable to provide a restriction so that frequencies can be suppressed only in these ranges.

It has been known that resonance in an ear resonance model using a simple common acoustic tube, high-order resonance occurs at a frequency of the integral multiple of the first-order resonance. That is, in an ear model using a simple common closed tube, the wavelength of sound resonating in the closed tube is represented as: $\lambda 1=2L$ for the first-order resonance, $\lambda 2=L=(1/2)\lambda 1$ for the second-order resonance, . . . , and $\lambda N=(2/N)L=(1/N)\lambda 1$ for the Nth-order resonance, where L is the length of the ear model. Thus, the relation can be represented as: the first-order resonant frequency $f1=v/\lambda 1$, the second-order resonant frequency $f2=v/\lambda 2=2(v/\lambda 1)=2*f1$, . . . , and the Nth-order resonant frequency $fN=v/\lambda N=N*(v/\lambda 1)=N*f1$, where v is the acoustic velocity. As described above, it is known that the second-order or higher resonant frequency is the integral multiple of the first-order resonant frequency f1.

On the other hand, according to the first embodiment, as illustrated in FIG. 6, the relation between the first-order resonant frequency (f1) and the second-order resonant frequency (f2) indicates a particular tendency different from that obtained by the ear resonance model using a simple common acoustic tube.

That is, it is hardly the case that the second-order resonant frequency f2 is just the double the first-order resonant frequency f1 (f2/f1=2), and inmost cases, f2/f1 is a non-integer less than 2. This is because, since the characteristics of the ear canal cannot be represented by the resonance of a simple closed tube, the resonant frequencies do not have an integral multiple relation but have a non-integral multiple relation. It is also found that, in most pieces of data, the second-order resonant frequencies are distributed in a range less than the double the first-order resonant frequencies ($1<f2/f1<2$). It can also be found from the distribution illustrated in FIG. 6 that, as the first-order resonant frequency increases, the ratio of the second-order resonant frequency and the first-order resonant frequency (f2/f1) tends to decrease.

Although FIG. 6 illustrates only an example of the relation between the first-order resonant frequency and the second-order resonant frequency, the measurement data indicates that the Nth-order resonant frequency of the human ear higher than the second-order resonant frequency highly tends to be lower than a value obtained by multiplying an integer N by the first-order resonant frequency and higher than a value obtained by multiplying (N−1) by the first-order resonant frequency. This can also be seen in the third-order resonance (left ear $f_{L3}$=about 18.2 Hz, right ear $f_{R3}$=about 16 Hz) illustrated in FIGS. 4 and 5. It is clearly found that the third-order resonance is tend to be less than a value triple (left ear: $f_{L3}$=about 18.2 Hz<3*$f_{L1}$=19.5 kHz) (right ear: $f_{R3}$=about 16 Hz<3*$f_{R1}$=18.3 kHz) of the first-order resonant frequency (left ear $f_{L1}$=about 6.5 kHz, right ear $f_{R1}$=about 6.1 kHz). It is also clearly found that the third-order resonance (left ear $f_{L3}$=about 18.2 Hz, right ear $f_{R3}$=about 16 Hz) is tend to be more than a value (left ear: $f_{L3}$=about 18.2 Hz>2*$f_{L1}$=13 kHz) (right ear: $f_{R3}$=about 16 Hz>2*$f_{R1}$=12.2 kHz) obtained by multiplying the first-order resonant frequency (left ear $f_{L1}$=about 6.5 kHz, right ear $f_{R1}$=about 6.1 kHz) by 2 (the order 3-1).

Accordingly, it can be supposed that not only the second-order resonant frequency, but also the Nth-order resonant frequency higher than the second-order resonant frequency highly tends to be lower than a value obtained by multiplying N by the first-order resonant frequency and higher than a value obtained by multiplying (N−1) by the first-order resonant frequency.

In the first embodiment, using the specific characteristics of ear resonance, the first-order resonance characteristics and the higher-order resonance characteristics occurring the real ear, which are in a non-integral multiple relation, are associated with each other to obtain pseudo anti-resonance characteristics. The pseudo anti-resonance characteristics are reflected in the compensation of resonance characteristics. Thus, the high-order resonance characteristics of the ear are effectively compensated, and acoustic signals can be reproduced in high quality without a feeling of ear-closing due to the resonance.

Regarding the pseudo anti-resonance, the first-order anti-resonant frequency is denoted by F1, while the second-order anti-resonant frequency is denoted by F2 using capital "F" to be differentiated from the first-order resonant frequency f1 and the second-order resonant frequency f2 measured in the real ear. It is desirable that the anti-resonant frequency and the resonant frequency of the real ear be in the following relation: F1=f1, F2=f2, if the earphones used for the measurement are placed in the ears under completely the same conditions. However, it is difficult to measure the resonant frequency of the real ear with earphones actually used by the user, and generally, the resonant frequency is measured with earphones other than those used by the user. Accordingly, the resonant frequency f1 (or f2) measured in the real ear does not always match the anti-resonant frequency F1 (or F2) related to the pseudo anti-resonance characteristics to be suitably applied to earphones used by the user to suppress the resonance. That is, f1 and f2 do not always match F1 and F2, respectively, and f1 and f2 need not necessarily match F1 and F2, respectively, as long as F1 and F2 corresponds to the pseudo anti-resonance characteristics suitable for the ears of the user and earphones used by the user. On the other hand, the characteristics of the mutual relation between the resonant frequencies (non-integral multiple relation and a range where non-integral multiple values exist) can be applied to the existing range of F1 and F2 on the frequency axis and their relation as with the existing range of f1 and f2 on the frequency axis and their relation. The same is true in other embodiments and modifications.

The acoustic signal compensator 150 of the first embodiment has the function of suppressing resonance using the unique characteristics of ear resonance.

The frequency characteristics for suppressing in advance resonance characteristics (resonance peaks) supposed to occur if compensation is not performed will be referred to as “pseudo anti-resonance characteristics”.

The pseudo anti-resonance characteristics are used to reduce the frequency amplitude of an acoustic signal around a resonance peak of the ear resonance that occurs in a space formed by the ear and an earphone placed in the ear. That is, the pseudo anti-resonance characteristics need not strictly be reverse characteristics of the resonance characteristics. The pseudo anti-resonance characteristics are only required to have such frequency characteristics as to reduce frequency amplitude around a resonance peak of the resonance characteristics supposed to occur unless compensation is performed. Specific examples of the pseudo anti-resonance characteristics will be described later.

Hereinafter, among the pseudo anti-resonance characteristics, a central frequency which is a reverse peak of the frequency amplitude or protrudes downward will be referred to as the pseudo anti-resonant frequency. The pseudo anti-resonant frequency includes the first to Nth-order pseudo anti-resonance characteristics in ascending order of frequency. That is, the first to Nth-order pseudo anti-resonance characteristics correspond to the first to Nth-order frequencies which is compensated to reduce a component of an acoustic signal.

To compensate the resonant frequency of the real ear having the characteristics as described above, the pseudo anti-resonance frequency is compensated in the same manner such that the second-order pseudo anti-resonant frequency is lower than the double of the first-order pseudo anti-resonant frequency. With this, the freedom of a range of selection of pseudo anti-resonant frequency can be effectively restricted. Accordingly, the acoustic signal compensator 150 of the first embodiment sets such restriction conditions to obtain the pseudo anti-resonant frequency. As to the ratio of the Nth-order pseudo anti-resonant frequency and the first-order pseudo anti-resonant frequency, by setting the same restriction conditions as those of the ratio of the Nth-order resonant frequency and the first-order resonant frequency, the freedom of a range of selection of pseudo anti-resonant frequency can be effectively restricted. Thus, it is possible to set the pseudo anti-resonant frequency restricted by the restriction conditions.

Further, the acoustic signal compensator 150 restricts the first-order pseudo anti-resonance characteristics and the Nth-order pseudo anti-resonance characteristics such that the Nth-order pseudo anti resonant frequency is lower than a value obtained by multiplying N by the first-order pseudo anti-resonant frequency and higher than a value obtained by multiplying (N−1) by the first-order pseudo anti-resonant frequency. The acoustic signal compensator 150 reflects the restricted first to Nth-order pseudo anti-resonance characteristics in an acoustic signal to compensate it. With this, the acoustic signal compensator 150 can effectively compensate even the high-order resonance characteristics of the real ear. Thus, the acoustic signal compensator 150 outputs the compensated acoustic signal in high sound quality not causing a feeling of ear-closing due to the resonance, unpleasant increased sound, and unnatural tone. In the following, a description will be given of the configuration of the acoustic signal compensator 150.

The acoustic signal receiving module 201 receives an acoustic signal from the acoustic signal generator (not illustrated) in the sound player 110.

The control receiver 205 receives a control instruction to the acoustic signal compensator 150 from the user. For example, the control receiver 205 may receive a control instruction to change the frequency to cancel the first to Nth-order resonance characteristics.

In the first embodiment, the control receiver 205 may receive various types of control instructions from the user to control the resonance characteristics. For example, the control receiver 205 may receive the value of the resonant frequency or information indicating the magnitude relation of frequencies as a control instruction.

The pseudo anti-resonance controller 204 is capable of receiving control from the outside to change the characteristics of the pseudo anti-resonance used in the compensator 202. The pseudo anti-resonance characteristics may be changed discretely or continuously. For example, to change the anti-resonant frequency related to the pseudo anti-resonance characteristics in response to a control instruction from the pseudo anti-resonance controller 204, a pseudo anti-resonance parameter is selected in a range defining the upper and lower limits of the frequencies F1 and F2 related to the first-order anti-resonance and the second-order anti-resonance so that the frequencies F1 and F2 can be changed in the range of existing frequencies determined for each of them.

As control information received by the control receiver 205, the pseudo anti-resonance controller 204 of the first embodiment outputs instruction information on the pseudo anti-resonant frequency to a pseudo anti-resonance parameter obtaining module 212. The pseudo anti-resonant frequency instructed by the instruction information may be only the first-order pseudo anti-resonant frequency or a combination of the first-order pseudo anti-resonant frequency and the Nth-order pseudo anti-resonant frequency. The pseudo anti-resonant frequency used for compensation can be obtained based on the output pseudo anti-resonant frequency and restrictions retained by a pseudo anti-resonant frequency restriction module 211.

If the resonant frequency is measured in advance using earphones with a microphone to measure the resonance for the acoustic signal compensator 150 of the first embodiment, the pseudo anti-resonance controller 204 may output instruction information on the pseudo anti-resonant frequency including the resonant frequency measured by the earphones to the pseudo anti-resonance parameter obtaining module 212.

The acoustic signal compensator 202 receives an acoustic signal from the acoustic signal receiving module 201 and compensates it. The acoustic signal compensator 202 then outputs the compensated acoustic signal to the output module 203.

The acoustic signal that the compensator 202 receives from the acoustic signal receiving module 201 may have undergone other acoustic processing such as low-frequency enhancement and various types of effects. Besides, the acoustic signal compensated by the compensator 202 may be subjected to other acoustic processing such as low-frequency enhancement and various types of effects, and then output to the output module 203. In both the cases, the same effect can be achieved, and obviously, the first embodiment includes such configurations.

The compensator 202 comprises the pseudo anti-resonance parameter determination module 210 and a resonance characteristic compensator 220.

The pseudo anti-resonance parameter determination module 210 comprises the pseudo anti-resonant frequency restriction module 211 and the pseudo anti-resonance parameter obtaining module 212. The pseudo anti-resonance parameter determination module 210 determines a pseudo anti-resonance parameter to suppress resonance characteristics and sets the pseudo anti-resonance parameter for the resonance characteristic compensator 220 to compensate the resonance characteristics.

Figure 7:
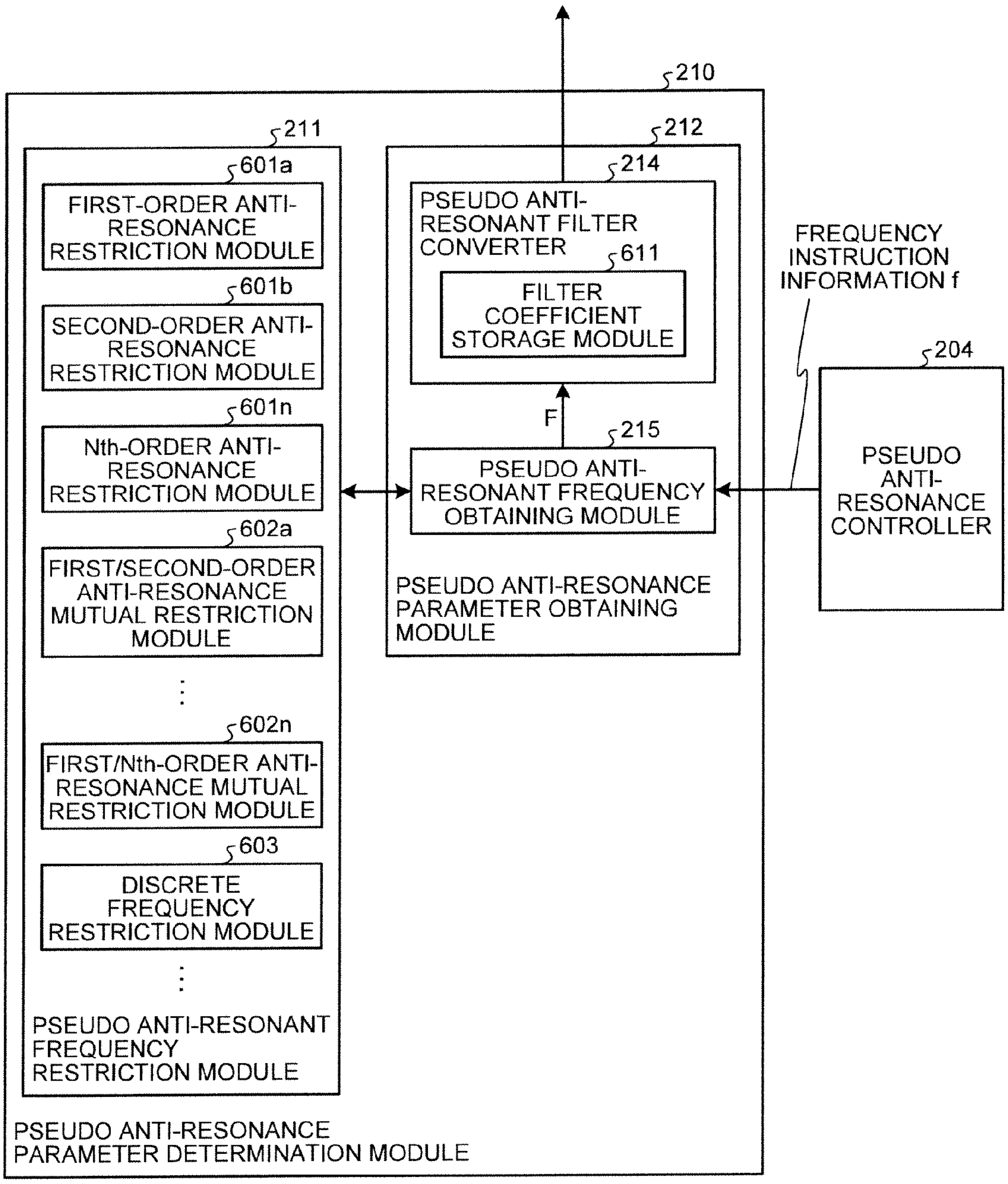
FIG. 7 is an exemplary detailed block diagram of a pseudo anti-resonance parameter determination module in the first embodiment.

FIG. 7 is a detailed block diagram of the pseudo anti-resonance parameter determination module 210. The pseudo anti-resonance parameter obtaining module 212 of the pseudo anti-resonance parameter determination module 210 comprises a pseudo anti-resonant frequency obtaining module 215 and a pseudo anti-resonant filter converter 214.

The pseudo anti-resonance parameter obtaining module 212 receives frequency instruction information f from the pseudo anti-resonance controller 204 and outputs it to the pseudo anti-resonant frequency obtaining module 215. The pseudo anti-resonant frequency obtaining module 215 restricts the frequency instruction information f using restriction related to the pseudo anti-resonance set by the pseudo anti-resonant frequency restriction module 211, which will be described later, based on the frequency instruction information f to obtain pseudo anti-resonant frequency instruction information F. The pseudo anti-resonant frequency obtaining module 215 outputs the pseudo anti-resonant frequency instruction information F to the pseudo anti-resonant filter converter 214.

The pseudo anti-resonant filter converter 214 converts a pseudo anti-resonant frequency contained in the pseudo anti-resonant frequency instruction information F received from the pseudo anti-resonant frequency obtaining module 215 to a filter coefficient of a filter (pseudo anti-resonant filter) having pseudo anti-resonance characteristics corresponding to the pseudo anti-resonant frequency.

The pseudo anti-resonant filter converter 214 sets the filter coefficient to the resonance characteristic compensator 220. In this manner, based on instruction information and frequency instruction information from the user, and characteristic instruction information from measurement results, it is possible to select a pseudo anti-resonance parameter necessary for compensation to reflect pseudo anti-resonance characteristics according to the instruction information in an acoustic signal (a parameter representing filter coefficient information if the compensation to reflect pseudo anti-resonance is performed by filtering).

As illustrated in FIG. 7, the pseudo anti-resonant frequency restriction module 211 comprises a first-order anti-resonance restriction module 601*a* to an Nth-order anti-resonance restriction module 601*n*, a first/second-order anti-resonance mutual restriction module 602*a* to a first/Nth-order anti-resonance mutual restriction module 602*n*, and a discrete frequency restriction module 603. In the first embodiment, among restriction conditions of the restriction modules of the pseudo anti-resonant frequency restriction module 211, the pseudo anti-resonant frequency obtaining module 215 is configured to refer to restrictions related to a frequency specified by the frequency instruction information f to obtain the pseudo anti-resonant frequency instruction information F by restricting the frequency instruction information f. However, this is by way of example only and other configurations may be employed as long as instruction information given to the pseudo anti-resonance parameter obtaining module 212 is compensated to be a combination of mutual relations of restricted resonant frequencies and a restricted frequency range reflecting restriction related to the resonant frequency of the ear.

In the first embodiment, regarding a frequency having pseudo anti-resonance characteristics frequency amplitude of which constitutes a reverse peak, the first-order pseudo anti-resonant frequency is denoted by F1, while the second-order pseudo anti-resonant frequency is denoted by F2 using capital "F". On the other hand, regarding a resonant frequency received through the pseudo anti-resonance controller 204 such as those measured in the real ear and received from the user, the first-order resonant frequency is denoted by f1, while the second-order resonant frequency is denoted by f2 using small "f" to be differentiated from the pseudo anti-resonant frequencies.

For example, the pseudo anti-resonant frequency restriction module 211 gives restriction conditions to the Kth (K=2, 3, . . . , N) order pseudo anti-resonant frequency for restricting the first to Nth-order pseudo anti-resonant frequencies based on the restriction conditions retained by the first/second-order anti-resonance mutual restriction module 602*a* to the first/Nth-order anti-resonance mutual restriction module 602*n* so that the Kth-order pseudo anti-resonant frequency is to be of a non-integral multiple of the first-order pseudo anti-resonant frequency lower than a value obtained by multiplying the first-order pseudo anti-resonant frequency by K, i.e., so that the ratio of the Kth-order pseudo anti-resonant frequency and the first-order pseudo anti-resonant frequency is lower than K (the Kth-order pseudo anti-resonant frequency/the first-order pseudo anti-resonant frequency<K).

To increase the accuracy of the restrictions, the pseudo anti-resonant frequency restriction module 211 may give restriction conditions to the Kth-order pseudo anti-resonant frequency so that the Kth-order pseudo anti-resonant frequency is to be of a non-integral multiple of the first-order pseudo anti-resonant frequency higher than a value obtained by multiplying the first-order pseudo anti-resonant frequency by (K−1), i.e., so that the ratio of the Kth-order pseudo anti-resonant frequency and the first-order pseudo anti-resonant frequency is higher than K−1 (the Kth-order pseudo anti-resonant frequency/first-order pseudo anti-resonant frequency<K−1).

FIG. 7 illustrates a specific example of a configuration in which the pseudo anti-resonance parameter determination module 210 determines a pseudo anti-resonance parameter used for compensation based on the frequency instruction information f received from the pseudo anti-resonance controller 204.

Incidentally, to measure the resonant frequency of the user's ear by earphones with a microphone for measurement, generally, the resonant frequency is not measured by the same earphones used by the user. Accordingly, the resonant frequency measured by earphones for measurement differs from the resonant frequency of the ear of the user wearing earphones that he/she generally uses.

For this reason, the first-order resonant frequency f1 (or the second-order resonant frequency f2) measured in the real ear does not always match the first-order pseudo anti-resonant frequency F1 (or the second-order pseudo anti-resonant frequency F2) related to the anti-resonance characteristics to suppress the resonance within the earphones used by the user. That is, the first-order resonant frequency f1 and the second-order resonant frequency f2 do not always match the first-order pseudo anti-resonant frequency F1 and the second-order pseudo anti-resonant frequency F2, respectively.

Further, the first-order resonant frequency f1 and the second-order resonant frequency f2 need not necessarily match the first-order pseudo anti-resonant frequency F1 and the second-order pseudo anti-resonant frequency F2, respectively. The first-order pseudo anti-resonant frequency F1 (or the second-order pseudo anti-resonant frequency F2) related to the anti-resonance characteristics to suppress the resonance in earphones used by the user may be any pseudo anti-resonant frequency related to pseudo anti-resonance characteristics for compensation to suppress an increase in the amplitude of an acoustic signal in a resonance peak frequency band that is supposed to occur if the compensation is not performed when the user wears the earphones.

Since the resonant frequency measured by earphones for measurement differs from the resonant frequency of the ear of the user wearing earphones that he/she generally uses, if the first-order pseudo anti-resonant frequency F1 and the second-order pseudo anti-resonant frequency F2 are directly applied to the first-order resonant frequency f1 and the second-order resonant frequency f2, respectively, assuming that F1=f1 and F2=f2, resonance cannot be improved that occurs when the user wears the earphones.

Meanwhile, regarding the first-order pseudo anti-resonant frequency F1, the second-order pseudo anti-resonant frequency F2, or higher-order pseudo anti-resonant frequencies, the characteristics of restrictions related to the existing range of resonant frequencies estimated from frequency distribution, restrictions related to the magnitude relation between the frequencies and the ratio of the frequencies, and restrictions related to the first-order pseudo anti-resonant frequency F1, the second-order pseudo anti-resonant frequency F2, or higher-order pseudo anti-resonant frequencies at the time of measurement in the real ear similarly arise from the principle of the resonance formed by the ear and an earphone. This characteristics can be used as restrictions upon obtaining a pseudo anti-resonance parameter. The first and following embodiments and modifications thereof use the characteristics and controls the characteristics based on the resonance restrictions in the real ear. Thus, it is possible to effectively obtain a resonant frequency (a pseudo anti-resonant frequency) for pseudo anti-resonance corresponding to resonance occurring when the user wears earphones that he/she generally uses. With this acoustic compensation using the pseudo anti-resonance characteristics, it is possible to easily and appropriately suppress resonance occurring when the user wears earphones that he/she generally uses.

That is, the acoustic signal compensator 150 is required to set not an actual resonant frequency but the first-order pseudo anti-resonant frequency F1 and the second-order pseudo anti-resonant frequency F2 near the actual resonant frequency. Accordingly, by restricting the existing range of the first-order pseudo anti-resonant frequency F1 and the second-order pseudo anti-resonant frequency F2 on the frequency axis, and their mutual relations, the first-order pseudo anti-resonant frequency F1 and the second-order pseudo anti-resonant frequency F2 can be easily derived.

It is assumed, for example, that the pseudo anti-resonance parameter determination module 210 receives the frequency instruction information f including a resonant frequency. As an example, if the frequency instruction information f includes the first to more than second-order resonant frequencies, the frequency instruction information f can be regarded as a vector. For example, if the first-order resonant frequency f1 and the second-order resonant frequency f2 are given, the frequency instruction information f can be represented as f=(f1, f2) using the resonant frequencies f1 and f2. The resonant frequencies applied to the frequency instruction information f are not limited to the first and the second-order resonant frequencies. The frequency instruction information f may be represented as f=(f1, f2, . . . , fn) using the first to Nth-order resonant frequencies.

The pseudo anti-resonance parameter obtaining module 212 outputs the frequency instruction information f received from the pseudo anti-resonance controller 204 to the pseudo anti-resonant frequency restriction module 211.

Having received the frequency instruction information f, the pseudo anti-resonant frequency restriction module 211 gives an instruction to the pseudo anti-resonance parameter obtaining module 212 so that the frequency instruction information f satisfies restriction conditions retained by the restriction modules of the pseudo anti-resonant frequency restriction module 211. According to the instruction, the pseudo anti-resonance parameter obtaining module 212 compensates the first-order resonant frequency f1 and the second-order resonant frequency f2 contained in the frequency instruction information f to satisfy the restriction conditions, thereby obtaining the first-order pseudo anti-resonant frequency F1 and the Nth-order pseudo anti-resonant frequency F2. The pseudo anti-resonance parameter obtaining module 212 may use the first to higher Nth-order resonant frequencies, and similarly obtains the first to Nth-order pseudo anti-resonant frequencies F1 to Fn. For example, when restricting the mutual relation between the first-order resonant frequency and the second-order resonant frequency, the pseudo anti-resonant frequency restriction module 211 gives a restriction or compensation instruction to the pseudo anti-resonance parameter obtaining module 212 (the pseudo anti-resonant frequency obtaining module 215) such that the second-order pseudo anti-resonant frequency F2 is to be of a non-integral multiple of the first-order pseudo anti-resonant frequency lower than the double of the first-order resonant frequency.

In the first embodiment, the second-order pseudo anti-resonance is higher than the first-order pseudo anti-resonance. In other words, it is defined that the second-order pseudo anti-resonance occurs as a frequency higher than the second-order pseudo anti-resonant frequency. Similarly, the third-order pseudo anti-resonance is higher than the second-order pseudo anti-resonance. In other words, it is defined that the third-order pseudo anti-resonance occurs as a frequency higher than the second-order pseudo anti-resonant frequency.

As the characteristics of the pseudo anti-resonance, for example, an anti-resonance peak frequency (second-order pseudo anti-resonant frequency) F2 having second-order pseudo anti-resonance characteristics is not a simple multiple of an anti-resonance peak frequency (first-order pseudo anti-resonant frequency) F1 having first-order pseudo anti-resonance characteristics. The second-order pseudo anti-resonant frequency F2 is lower than the double of the first-order pseudo anti-resonant frequency F1.

The acoustic signal compensator 150 of the first embodiment compensates an acoustic signal using pseudo anti-resonance characteristics taking into account the second-order and higher resonant frequencies. Thus, the acoustic signal compensator 150 performs the compensation more suitable for resonance in the real ear.

The first-order anti-resonance restriction module **601*a* to the Nth-order anti-resonance restriction module 601*n* give a restriction instruction to the pseudo anti-resonance parameter obtaining module 212 (the pseudo anti-resonant frequency obtaining module 215) so that the first to Nth-order anti-resonant frequencies are higher than 5 kHz. This is based on that the earphone 120 of the first embodiment is a canal type earphone, and measurement results indicating that, in the case of a canal type earphone, a resonance peak occurs at a frequency of 5 kHz or higher. This can be seen from FIG. 6 indicating data obtained by measurement in the ears of various users, in which the first-order resonant frequencies f1** on the horizontal axis are distributed at frequencies of 5 kHz and higher. Thus, it is possible to derive a pseudo anti-resonant frequency in an appropriate existing range.

When a received resonant frequency is changed to a pseudo anti-resonant frequency having pseudo anti-resonance characteristics, the resonant frequency can be changed within a range determined in advance for the first-order pseudo anti-resonant frequency and the second-order pseudo anti-resonant frequency. Accordingly, the first-order anti-resonance restriction module 601*a* to the Nth-order anti-resonance restriction module 601*n* give a restriction or compensation instruction to the pseudo anti-resonance parameter obtaining module 212 (the pseudo anti-resonant frequency obtaining module 215) so that the pseudo anti-resonant frequency is to be obtained in a range defined by the upper and lower limits.

More specifically, the first-order anti-resonance restriction module 601*a* to the Nth-order anti-resonance restriction module 601*n* retain the existing range of a specific pseudo anti-resonant frequency with respect to each order. The existing range represents the range of a pseudo anti-resonant frequency of each order effective to suppress ear resonant component of the order. For example, the first-order anti-resonance restriction module 601*a* retains the existing range of the first-order resonant frequency effective to suppress the first-order ear resonant component. The first-order anti-resonance restriction module 601*a* compares the existing range with the first-order resonant frequency f1 contained in the frequency instruction information f. As a result of the comparison, if determining that the first-order resonant frequency f1 is out of the existing range, the first-order anti-resonance restriction module 601*a* gives a restriction or compensation instruction to the pseudo anti-resonance parameter obtaining module 212 (the pseudo anti-resonant frequency obtaining module 215) so that the first-order resonant frequency f1 is included in the existing range.

The first-order anti-resonance restriction module 601*a* of the first embodiment restricts or compensates a resonant frequency based on the distribution of first-order resonant frequencies derived from the analysis of measurement data obtained from the ears of various users as illustrated in FIG. 6 so that the first-order pseudo anti-resonant frequency is included in a range of about 5 kHz to 10 kHz.

Similarly, the second-order anti-resonance restriction module 601*b* retains the existing range of the second-order resonant frequency effective to suppress the second-order ear resonant component. The second-order anti-resonance restriction module 601*b* compares the existing range with the second-order resonant frequency f2 contained in the frequency instruction information f. As a result of the comparison, if determining that the second-order resonant frequency f2 is out of the existing range, the second-order anti-resonance restriction module 601*b* gives a restriction or compensation instruction to the pseudo anti-resonance parameter obtaining module 212 (the pseudo anti-resonant frequency obtaining module 215) so that the second-order resonant frequency f2 is included in the existing range.

The second-order anti-resonance restriction module 601*b* of the first embodiment restricts or compensates a resonant frequency based on the distribution of second-order resonant frequencies derived from the analysis of measurement data obtained from the ears of various users as illustrated in FIG. 6 so that the second-order pseudo anti-resonant frequency is included in a range of about 9 kHz to 15 kHz.

The first/second-order anti-resonance mutual restriction module 602*a* to the first/Nth-order anti-resonance mutual restriction module 602*n* retain restrictions related to the mutual relation between the first-order resonant frequency and the second to Nth-order resonant frequencies. For example, the first/second-order anti-resonance mutual restriction module 602*a* retains and stores restrictions related to the mutual relation between the first-order resonant frequency and the second-order resonant frequency. The first/second-order anti-resonance mutual restriction module 602*a* compares the restrictions with first and second-order frequency information contained in the frequency instruction information f. As a result of the comparison, if determining that the first-order resonant frequency and the second-order resonant frequency are out of the restrictions, the first/second-order anti-resonance mutual restriction module 602*a* restricts or compensates the resonant frequency to satisfy the restrictions.

For example, the first/second-order anti-resonance mutual restriction module 602*a* retains, as a restriction condition, a frequency range of the second-order resonant frequency $f2=\alpha2*f1$, where f1 is the first-order resonant frequency and the range of $\alpha2$ is $1<\alpha2<2$, i.e., a frequency range in which the second-order resonant frequency is higher than the first-order resonant frequency and lower than the double of the first-order resonant frequency. The first/second-order anti-resonance mutual restriction module 602*a* restricts or compensates the second-order resonant frequency f2 or the first-order resonant frequency f1 so that the resonant frequencies are not to be out of the frequency range set as a restriction condition. The first/second-order anti-resonance mutual restriction module 602*a* may restrict or compensate the second-order resonant frequency f2 or the first-order resonant frequency f1 so that the second-order resonant frequency f2 is in a range above the first-order resonant frequency f1+3 kHz and below f1+7 kHz.

A reference frequency Fm may be set as reference in the first/second-order anti-resonance mutual restriction module 602*a*. In this case, depending on whether the first-order resonant frequency is higher than the reference frequency Fm, the first/second-order anti-resonance mutual restriction module 602*a* changes the compensation processing on the second-order resonant frequency or the first-order resonant frequency. For example, it is assumed that the reference frequency Fm is 7500 kHz. If the first-order resonant frequency f1 is lower than the reference frequency Fm, the first/second-order anti-resonance mutual restriction module 602*a* restricts or compensates the second-order resonant frequency f2 or the first-order resonant frequency f1 so that $a*f1\leqq f2<b*f1$ (a=1.5, b=2). On the other hand, if the first-order resonant frequency f1 is higher than the reference frequency Fm, the first/second-order anti-resonance mutual restriction module 602*a* restricts or compensates the second-order resonant frequency f2 or the first-order resonant frequency f1 so that $a*f1\leqq f2<b*f1$ (a=1.3, b=1.9). The reference frequency and equations are cited above by way of example, and other examples may be employed.

These compensations are based on the tendency indicated by FIG. 6. That is, there is a tendency that the higher the first-order resonant frequency f1 is, the smaller the ratio of the second-order resonant frequency f2 and the first-order resonant frequency f1 (f2/f1) is (as a broad tendency, referring to data distributions plotted in FIG. 6, as the first-order resonant frequency f1 gets higher, the ratio of (f2/f1) gets smaller). On the basis of around the reference frequency, the distribution of ratios of frequencies f1 and f2 differs a little between when the first-order resonant frequency is high and when it is low. More specifically, on the basis of around the reference frequency, when the first-order resonant frequency is lower than the reference frequency, the most of ratios of (f2/f1) distribute in a range above 1.5 and below 2. On the other hand, on the basis of around the reference frequency, when the first-order resonant frequency is higher than the reference frequency, ratios of (f2/f1) distribute in a range above 1.3 and below 1.9, and there is found a tendency that the range becomes smaller.

Accordingly, the first/second-order anti-resonance mutual restriction module 602*a* restricts the second-order pseudo anti-resonant frequency so that it is a first non-integral multiple of the first-order pseudo anti-resonant frequency when the first-order pseudo anti-resonant frequency is lower than the reference frequency. The first/second-order anti-resonance mutual restriction module 602*a* restricts the second-order pseudo anti-resonant frequency so that it is a second non-integral multiple of the first-order pseudo anti-resonant frequency when the first-order pseudo anti-resonant frequency is higher than the reference frequency. In the restriction, the second non-integral multiple is smaller than the first non-integral multiple. With the restrictions of the first/second-order anti-resonance mutual restriction module 602*a*, as the first-order pseudo anti-resonant frequency is higher, the ratio of the second-order pseudo anti-resonant frequency component of which is to be suppressed and the first-order pseudo anti-resonant frequency is made smaller.

The first/second-order anti-resonance mutual restriction module 602*a* issues an instruction to restrict or compensate a resonant frequency based on a restriction that as the first-order resonant frequency exceeds the reference frequency, the ratio of the second-order resonant frequency to the first-order resonant frequency, i.e., the ratio (f2/f1) of f2 to f1, becomes smaller. With this, the pseudo anti-resonant frequency obtaining module 215 obtains pseudo anti-resonant frequencies (the first-order pseudo anti-resonant frequency and the second-order pseudo anti-resonant frequency).

In the first embodiment, even if the frequency instruction information f includes only the first-order resonant frequency f1, a pseudo anti-resonant frequency F2 can be obtained based on a restriction condition retained by the first/second-order anti-resonance mutual restriction module 602*a*. In this case, the first/second-order anti-resonance mutual restriction module 602*a* retains, as a restriction condition, F2=c*F1 or F2=c*f1 (parameter c is determined in advance and a non-integer greater than 1 and less than 2 as described above), and obtains a pseudo anti-resonant frequency F2 using the obtained first-order resonant frequency f1 or F1. The obtained pseudo anti-resonant frequency F2 may be compensated to satisfy other restriction conditions.

For another example, the mutual relation between F1 and F2 may be defined using a function c(F1) where the value of F1 is variable, such as F2=c(F1)*F1. In this case, a set of frequencies F1 and F2 can be obtained while the mutual relation between F1 and F2 or F1 and (F2/F1) is represented by a flexible non-linear relation.

With this configuration, if the pseudo anti-resonant frequency F1 suitable for the user is selected by, for example, controlling the first-order resonant frequency f1 or the pseudo anti-resonant frequency F1, the second-order pseudo anti-resonant frequency F2 is automatically determined simultaneously with the selection of the first-order pseudo anti-resonant frequency F1. This eliminates the need to control the second-order pseudo anti-resonant frequency F2. Thus, the number of combinations of the first-order pseudo anti-resonant frequency F1 and the second-order pseudo anti-resonant frequency F2 can be effectively reduced. As a result, it is possible to reduce the creation of a pseudo anti-resonance parameter and a memory capacity necessary to store the pseudo anti-resonance parameter. Further, complications to determine the pseudo anti-resonance parameter can be reduced to a large extent.

The first/Nth-order anti-resonance mutual restriction module 602*n* operates in the same manner as the first/second-order anti-resonance mutual restriction module 602*a*. Even if the frequency instruction information f does not include the Nth-order resonant frequency f1, the first/Nth-order anti-resonance mutual restriction module 602*n* can derive the Nth-order resonant frequency fN or the Nth-order pseudo anti-resonant frequency FN from the first-order resonant frequency f1 or the first-order pseudo anti-resonant frequency F1 and a retained restriction condition (for example, fN is lower than a value obtained by multiplying the first-order resonant frequency f1 by N, the Nth-order pseudo anti-resonant frequency FN is lower than a value obtained by multiplying the first-order pseudo anti-resonant frequency F1 by N, or (fN/f2) or (FN/F1) is a non-integer less than N). As described above, higher resonance can be obtained and compensated in the same manner as the second resonance.

If the frequency instruction information f is out of the range of resolution of discrete frequencies considered to be acceptable by the pseudo anti-resonant filter converter 214, the discrete frequency restriction module 603 gives a restriction or compensation instruction to the pseudo anti-resonance parameter obtaining module 212 (the pseudo anti-resonant frequency obtaining module 215) so that the frequency instruction information f is of the resolution of a discrete frequency considered to be acceptable by the pseudo anti-resonant filter converter 214.

In the first embodiment, the existing range of each pseudo anti-resonant frequency and the mutual relation between pseudo anti-resonances are stored in advance as restriction conditions to select a pseudo anti-resonant frequency, and the frequency is compensated. Thus, it is possible to effectively set a compensation suitable for the ear of the user wearing earphones.

In this manner, the pseudo anti-resonant frequency restriction module 211 gives a restriction or compensation instruction to the pseudo anti-resonance parameter obtaining module 212 (the pseudo anti-resonant frequency obtaining module 215) as to each resonant frequency included in the frequency instruction information f. The pseudo anti-resonance parameter obtaining module 212 (the pseudo anti-resonant frequency obtaining module 215) sets a resonant frequency obtained according to the restriction or compensation instruction as a pseudo anti-resonant frequency. In this manner, the pseudo anti-resonant frequency obtaining module 215 restricts or compensates the frequency instruction information f, and the resultant F is represented as F=Constraint (f). The Constraint ( ) represents the function of restrictions related to the pseudo anti-resonant frequency defined by the pseudo anti-resonant frequency restriction module 211.

The pseudo anti-resonant filter converter 214 converts the frequency instruction information F restricted or compensated by the pseudo anti-resonant frequency obtaining module 215 to coefficient information of a pseudo anti-resonant filter used for compensation. The pseudo anti-resonant filter converter 214 comprises a filter coefficient storage module 611. For example, the pseudo anti-resonant filter converter 214 stores in advance coefficient information of pseudo anti-resonant filters corresponding to a range of pseudo anti-resonant frequencies that satisfy the restriction conditions of the pseudo anti-resonant frequency restriction module 211 and information on the pseudo anti-resonant frequencies in the filter coefficient storage module 611. The pseudo anti-resonant filter converter 214 reads coefficient information of a pseudo anti-resonant filter corresponding to a pseudo anti-resonant frequency that matches or is the closest to pseudo anti-resonant frequency information related to the frequency instruction information F. The pseudo anti-resonant filter converter 214 outputs the coefficient information to the resonance characteristic compensator 220 (FIG. 3) as information of a pseudo anti-resonant filter converted from the frequency instruction information F.

Examples of pseudo anti-resonance parameters as compensation parameters to suppress resonance include obtained frequencies F1 and F2 related to pseudo anti-resonance, higher-order pseudo anti-resonant frequencies, and filter coefficient of a filter representing pseudo anti-resonance characteristics (pseudo anti-resonant filter). For example, among filters representing pseudo anti-resonance characteristics, a filter P1(z, F1) representing first-order pseudo anti-resonance characteristics and a filter P2(z, F2) representing second-order pseudo anti-resonance characteristics can be designed by a known method. In other words, by a known method, it is possible to design a filter having such characteristics that, with the first-order pseudo anti-resonant frequency F1 and the second-order pseudo anti-resonant frequency F2 as central frequencies of pseudo anti-resonance characteristics, respectively, the frequency amplitude is a reverse peak or the frequency amplitude is suppressed in the pseudo anti-resonance characteristics F1 and F2.

Anti-resonance characteristic filters thus designed are set to a first-order anti-resonance characteristic assignment module 221*a*, a second-order anti-resonance characteristic assignment module 221*b*, . . . , and an Nth-order anti-resonance characteristic assignment module 221*n*, respectively. Filtering is performed on an input acoustic signal, and thereby compensation based on a total of first to high-order pseudo anti-resonance characteristics are reflected in the acoustic signal.

In the first embodiment, an example is described in which the pseudo anti-resonant filter converter 214 stores in advance coefficient information of pseudo anti-resonance characteristic filters. For another example, the filter coefficient of a band-reject filter to suppress frequency characteristics may be dynamically calculated for the frequency band of the pseudo anti-resonant frequency corresponding to obtained pseudo anti-resonant frequency information instead of selecting coefficient information of a pseudo anti-resonance characteristic filter stored in advance. In this case, it is possible to reduce memory capacity required to store the coefficient information of pseudo anti-resonance characteristic filters. The band-reject filter can be designed by a known method.

FIGS. 8 to 12 illustrate examples of pseudo anti-resonance characteristic filters used in the resonance characteristic compensator 220. FIGS. 8 to 12 illustrate the first-order pseudo anti-resonant frequency F1 and the second-order pseudo anti-resonant frequency F2 obtained by the pseudo anti-resonant frequency obtaining module 215 and used in the resonance characteristic compensator 220. Further, FIGS. 8 to 12 illustrate examples of the first-order resonant frequency f1 and the second-order resonant frequency f2 that constitute resonance peaks when measurement is performed in the ear of the user wearing earphones for measurement. FIGS. 8 to 12 illustrate examples of anti-resonance characteristics when the first-order resonant frequency f1 and the second-order resonant frequency f2 do not match the first-order pseudo anti-resonant frequency F1 and the second-order pseudo anti-resonant frequency F2, respectively.

As described above, it is difficult to measure the resonant frequency of the real ear with earphones used by the user, and generally, the resonant frequency is measured with earphones other than those used by the user. Accordingly, the first-order resonant frequency f1 and the second-order resonant frequency f2 do not always match the first-order pseudo anti-resonant frequency F1 and the second-order pseudo anti-resonant frequency F2, respectively.

According to the first embodiment, regarding the existing range of the first-order pseudo anti-resonant frequency F1 and the second-order pseudo anti-resonant frequency F2 on the frequency axis and their relation, the existing range of the first-order resonant frequency f1 and the second-order resonant frequency f2 on the frequency axis and their relation are used to determine the first-order pseudo anti-resonant frequency F1 and the second-order pseudo anti-resonant frequency F2. Therefore, if the first-order resonant frequency f1 and the second-order resonant frequency f2 do not match the first-order pseudo anti-resonant frequency F1 and the second-order pseudo anti-resonant frequency F2, respectively, pseudo anti-resonance characteristics suitable for earphones used by the user and user's ears can be generated or selected. FIGS. 8 to 12 illustrate examples of anti-resonance characteristics when the first-order resonant frequency f1 and the second-order resonant frequency f2 do not match the first-order pseudo anti-resonant frequency F1 and the second-order pseudo anti-resonant frequency F2, respectively. As can be seen from FIGS. 8 to 12, by selecting such pseudo anti-resonance characteristics as to suppress the frequency amplitude around the pseudo anti-resonant frequencies F1 and F2, even if the pseudo anti-resonant frequencies F1 and F2 do not match the resonant frequencies f1 and f2 measured in the real ear, the resonant frequencies are suppressed. Thus, the resonance can be compensated using the pseudo anti-resonance characteristics. Further, although the ear resonance frequency varies to some extent depending on earphones in use, the resonant frequencies can be suppressed using pseudo anti-resonant frequencies, and thereby the resonance can be compensated.

Figure 8:
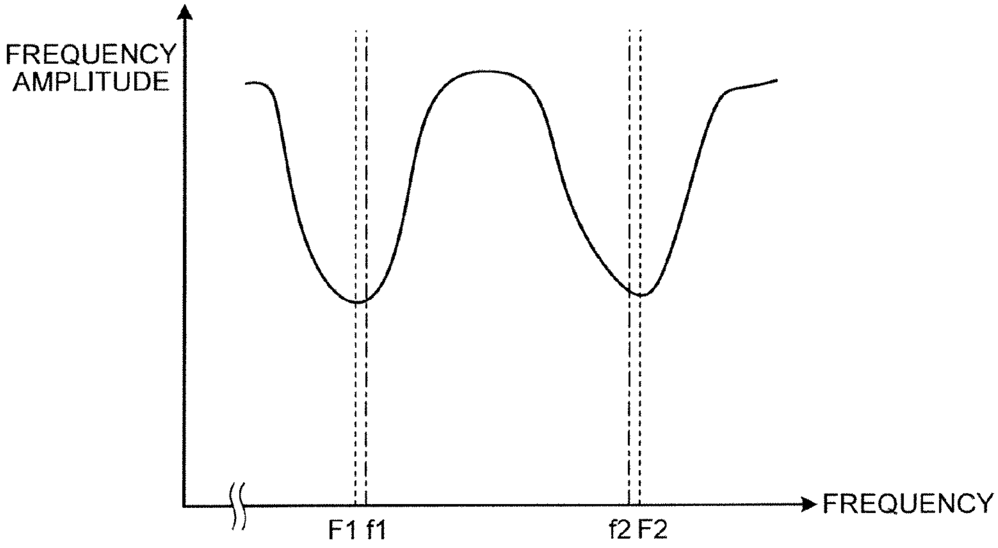
FIGS. 8 to 12 are exemplary graphs of frequency characteristics containing a first-order pseudo anti-resonant frequency F1 and a second-order pseudo anti-resonant frequency F2 obtained by a pseudo anti-resonant frequency obtaining module and used in a resonance characteristic compensator in the first embodiment.

FIG. 8 illustrates an example in which the first-order resonant frequency f1 and the second-order resonant frequency f2 are close to some extent to the first-order pseudo anti-resonant frequency F1 and the second-order pseudo anti-resonant frequency F2, respectively. As can be seen from FIG. 8, anti-resonance characteristics work on frequencies around the first-order resonant frequency f1 and the second-order resonant frequency f2 using pseudo anti-resonance characteristics that the frequency amplitude is a reverse peak or the frequency amplitude is suppressed at the first-order pseudo anti-resonant frequency F1 and the second-order pseudo anti-resonant frequency F2. Thus, it is possible to generate an acoustic signal where ear resonance supposed to occur unless compensated is compensated before it occurs using pseudo anti-resonance characteristics.

Figure 9:
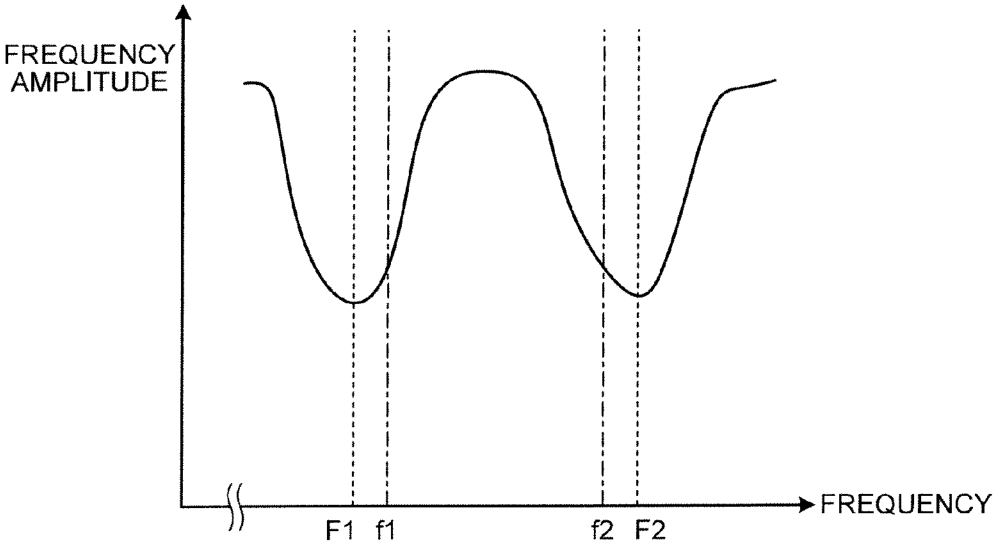

While FIG. 8 illustrates an example in which the resonance peak frequency f1 (or f2) is close to the pseudo anti-resonance reverse peak frequency F1 (or F2), it is not so limited. FIG. 9 illustrates an example in which the first-order resonant frequency f1 and the second-order resonant frequency f2 are not close to but different to some extent from the first-order pseudo anti-resonant frequency F1 and the second-order pseudo anti-resonant frequency F2, respectively. In this case also, the frequency amplitude of an acoustic signal can be suppressed to compensate resonance peaks around the first-order resonant frequency f1 and the second-order resonant frequency f2 supposed to occur unless compensated.

Figure 10:
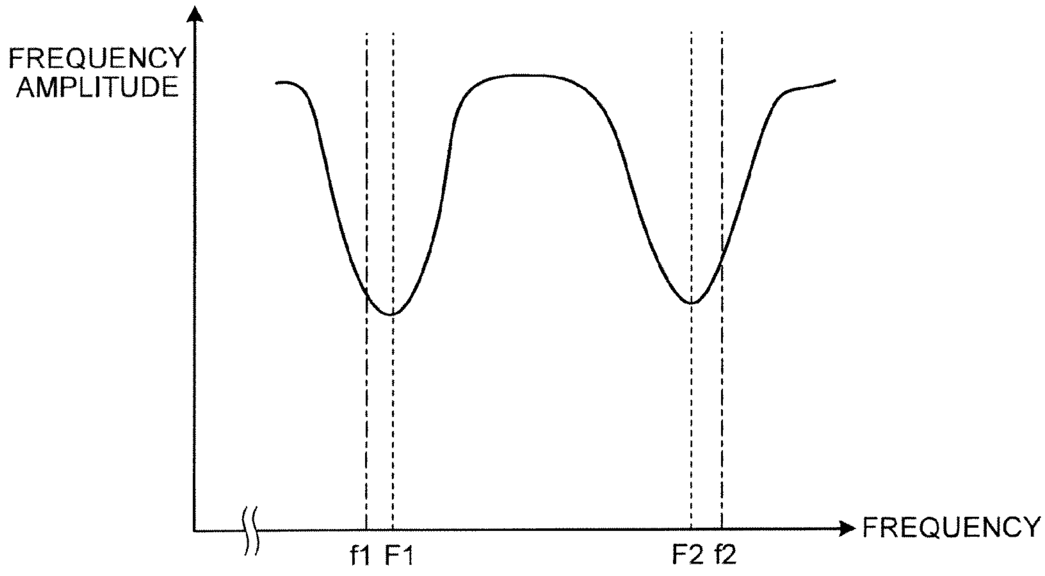

While FIG. 9 illustrates the case where the first-order resonant frequency f1>the first-order pseudo anti-resonant frequency F1 and the second-order resonant frequency f2<the second-order pseudo anti-resonant frequency F2, it is not so limited. The same is applied to the case where the first-order resonant frequency f1<the first-order pseudo anti-resonant frequency F1 and the second-order resonant frequency f2>the second-order pseudo anti-resonant frequency F2 as illustrated in FIG. 10.

Figure 11:
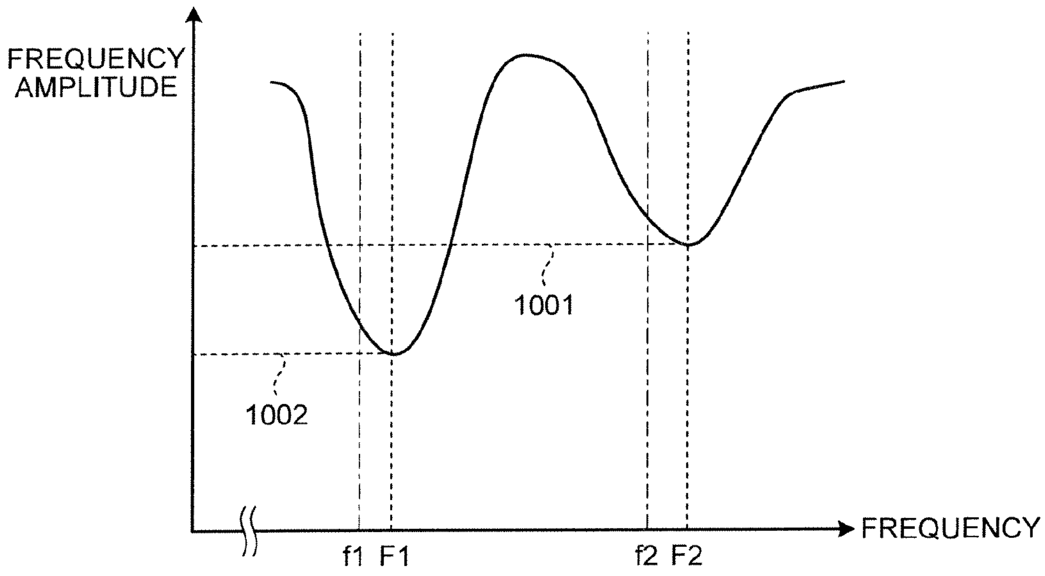

Further, as illustrated in FIG. 11, in pseudo anti-resonance characteristics, the amplitude may vary depending on each pseudo anti-resonant frequency. FIG. 11 illustrates an example in which, regarding pseudo anti-resonance characteristics, a frequency amplitude 1002 at the first-order pseudo anti-resonant frequency F1 is suppressed more than a frequency amplitude 1001 at the second-order pseudo anti-resonant frequency F2. In this manner, the amount of suppression may be varied for each order depending on the resonance peak amplitude. With this, appropriate compensation can be performed according to the intensity of resonance that varies depending on the resonant order or user's preference.

Figure 12:
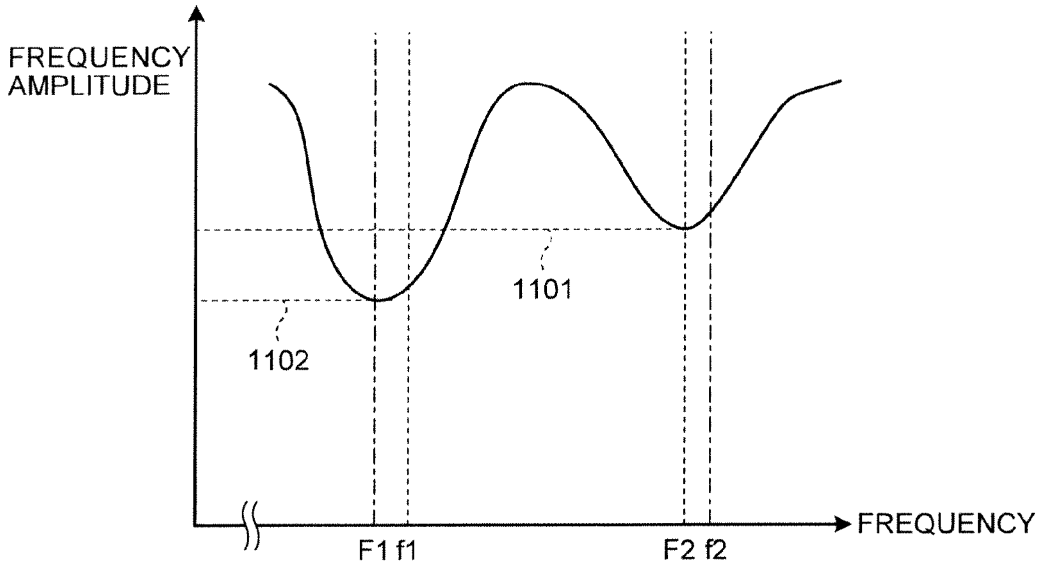

While FIG. 11 illustrates the case where the first-order resonant frequency f1<the first-order pseudo anti-resonant frequency F1 and the second-order resonant frequency f2>the second-order pseudo anti-resonant frequency F2, it is not so limited. The same is applied to the case where the first-order resonant frequency f1>the first-order pseudo anti-resonant frequency F1 and the second-order resonant frequency f2>the second-order pseudo anti-resonant frequency F2 as illustrated in FIG. 12.

Whether a pseudo anti-resonant frequency is in the range where it effectively works on a resonant frequency can be determined based on, for example, whether the pseudo anti-resonant frequency (=the central frequency at which the frequency amplitude of pseudo anti-resonance characteristics protrudes downward or a frequency at which the frequency amplitude of pseudo anti-resonance characteristics represents a reverse peak) covers the resonance peak of the resonant frequency. If the pseudo anti-resonant frequency can effectively reduce volume increase due to resonance that occurs in a space formed by the ear and earphones or headphones, the pseudo anti-resonant frequency is in the range where it effectively works on the resonant frequency of resonance that occurs in a space formed by the ear and earphones or headphones.

If a pseudo anti-resonant frequency is out of the range where it effectively works on a resonant frequency, the pseudo anti-resonant frequency cannot effectively reduce volume increase due to resonance that occurs in a space formed by the ear and earphones or headphones. Besides, change in pseudo anti-resonance characteristics is recognized, and it seems better not to perform compensation. Accordingly, whether a pseudo anti-resonant frequency is in the range where it effectively works on a resonant frequency can be determined based also on this.

As illustrated in FIGS. 8 to 12, the resonance characteristic compensator 220 performs compensation processing on an acoustic signal to reflect such pseudo anti-resonance characteristics as to suppress the frequency amplitude with each pseudo anti-resonant frequency as a reverse peak. Besides the filtering as described above, conversion such as discrete cosine transform (DCT), fast Fourier transform (FFT) may be performed to convert an acoustic signal to a conversion domain (or a frequency domain). In this case, components of the converted acoustic signal are multiplied by characteristics of the conversion domain of pseudo anti-resonance (or frequency characteristics) in the conversion domain (or the frequency domain), and the conversion domain (or the frequency domain) is converted to a time domain.

As described above, it is difficult to measure the resonant frequency of the real ear of the user wearing earphones with the earphones used by the user. As can be seen from FIGS. 8 to 12, since the frequency amplitude is suppressed around a pseudo anti-resonant frequency, even if not matching a resonant frequency measured in the real ear, the pseudo anti-resonant frequency works on the resonant frequency to suppress it. Thus, the resonance can be compensated.

Further, although the ear resonance frequency varies to some extent depending on earphones in use, the resonant frequencies can be suppressed using a pseudo anti-resonant frequency selectable from a restricted range. Thus, the resonance can be compensated.

The pseudo anti-resonant filter converter 214 sets the coefficient information of the pseudo anti-resonant filter converted from the frequency instruction information F to the resonance characteristic compensator 220 (the first-order anti-resonance characteristic assignment module 221*a*, the second-order anti-resonance characteristic assignment module 221*b*, . . . , and the Nth-order anti-resonance characteristic assignment module 221*n*).

Referring back to FIG. 3, the resonance characteristic compensator 220 has the function of reflecting the first to Nth-order pseudo anti-resonance characteristics in an input acoustic signal.

For example, the resonance characteristic compensator 220 compensates an input acoustic signal to suppress the amplitude (components) of the first-order pseudo anti-resonant frequency and the second-order pseudo anti-resonant frequency that is higher than the first-order pseudo anti-resonant frequency and lower than the double thereof according to the set pseudo anti-resonant filter.

Regarding the second to Nth-order pseudo anti-resonant frequency, the resonance characteristic compensator 220 performs compensation in the same manner as described above. For example, the resonance characteristic compensator 220 compensates an input acoustic signal to suppress the amplitude (components) of the first-order pseudo anti-resonant frequency and the Nth-order pseudo anti-resonant frequency that is lower than a value obtained by multiplying an integer N (N: an integer 2 or more) by the first-order resonant frequency and higher than a value obtained by multiplying (N−1) by the first-order resonant frequency according to the set pseudo anti-resonant filter. In the first embodiment, for example, the resonance characteristic compensator 220 is configured to comprise the first-order anti-resonance characteristic assignment module 221*a*, the second-order anti-resonance characteristic assignment module 221*b*, . . . , and the Nth-order anti-resonance characteristic assignment module 221*n* for the compensation.

The first-order anti-resonance characteristic assignment module 221*a*, the second-order anti-resonance characteristic assignment module 221*b*, . . . , and the Nth-order anti-resonance characteristic assignment module 221*n* compensate an acoustic signal to suppress the frequency amplitudes of the first-order pseudo anti-resonant frequency F1 to the Nth-order pseudo anti-resonant frequency Fn based on the coefficient information of the pseudo anti-resonant filters set for the respective orders.

The first-order anti-resonance characteristic assignment module 221*a*, the second-order anti-resonance characteristic assignment module 221*b*, . . . , and the Nth-order anti-resonance characteristic assignment module 221*n* compensate an acoustic signal to reflect the restriction conditions related to the first to Nth pseudo anti-resonance characteristics (N≧2) as described above in the frequency band of the acoustic signal higher than 5 kHz.

In the first embodiment, the first-order anti-resonance characteristic assignment module 221*a*, the second-order anti-resonance characteristic assignment module 221*b*, . . . , and the Nth-order anti-resonance characteristic assignment module 221*n* can perform the compensation in any order. This is because, if there is a change in the order of processes with the respective filters, the total characteristics do not change if the filters are linear filters. Thus, the filtering processes can be performed in any order with the same effect.

An acoustic signal received by the resonance characteristic compensator 220 will be denoted by x(n). The filtering processes performed as compensation by the first-order anti-resonance characteristic assignment module 221*a*, the second-order anti-resonance characteristic assignment module 221*b*, . . . , and the Nth-order anti-resonance characteristic assignment module 221*n* of the resonance characteristic compensator 220 will be collectively referred to for simplicity as "filter coefficient c(i)" (i=0, 1, . . . , and M−1, where M is the order of the filter). An acoustic signal y(n) output from the resonance characteristic compensator 220 can be generated by the filtering process represented by the following Equation 1:

$$y(n) = \sum_{i=0}^{M-1} c(i)x(n-i) \tag{1}$$

The output module 203 outputs the acoustic signal compensated by the resonance characteristic compensator 220 to the earphone 120. That is, the output module 203 reproduces the acoustic signal compensated by the resonance characteristic compensator 220 through the earphone 120. While the output module 203 generally outputs audio signals of two, left (L) and right (R), channels, an acoustic signal to be compensated may be a monaural signal. It may suffice if signals appropriately compensated with respect to channels necessary for reproduction are reproduced and output.

Figure 13:
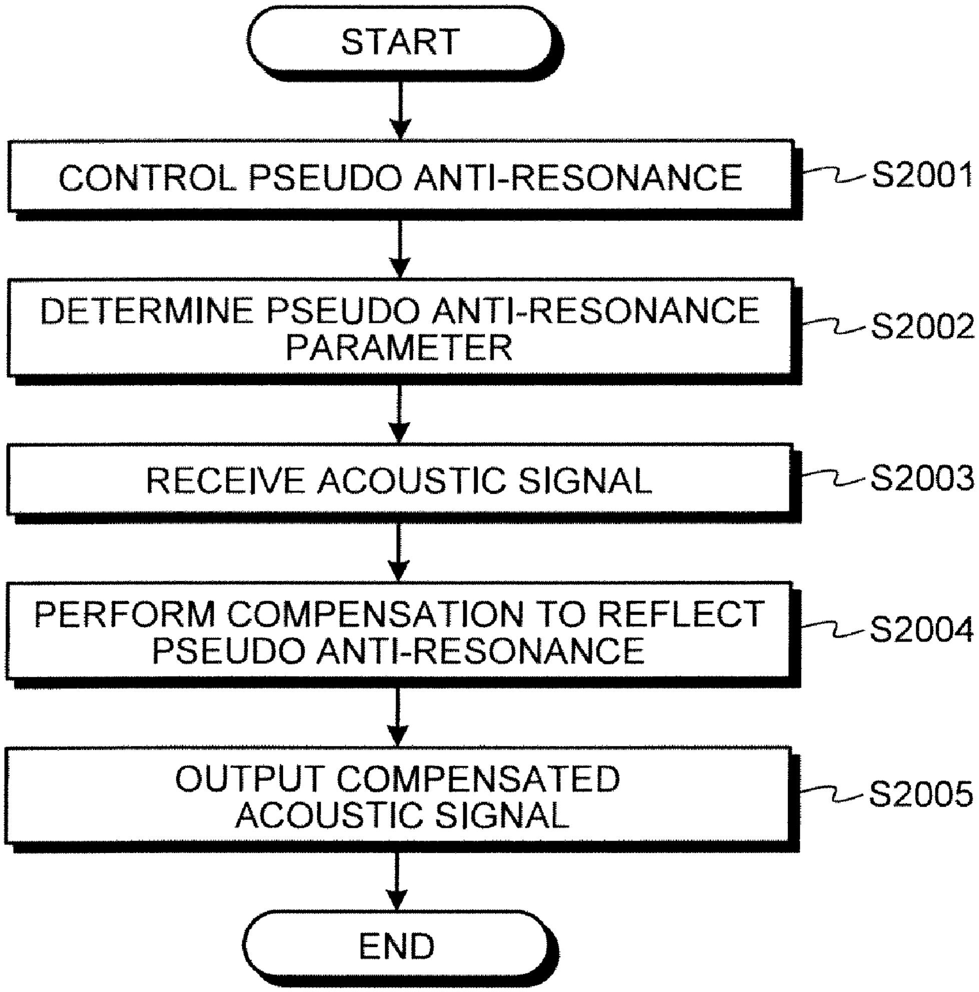
FIG. 13 is an exemplary flowchart of the operation of an acoustic signal compensator in the first embodiment.

A description will now be given of the operation of the acoustic signal compensator 150 to compensate an acoustic signal according to the first embodiment. FIG. 13 is a flowchart of the operation of the acoustic signal compensator 150 to compensate an acoustic signal according to the first embodiment.

First, the pseudo anti-resonance controller 204 controls pseudo anti-resonance in the pseudo anti-resonance parameter determination module 210 based on instruction information for pseudo anti-resonance characteristics received by the control receiver 205 (S2001).

Under the control of the pseudo anti-resonance controller 204, the pseudo anti-resonance parameter determination module 210 restricts a pseudo anti-resonant frequency to a restricted range according to the restrictions related to the pseudo anti-resonant frequency in response to the instruction information for the pseudo anti-resonance characteristics. Thus, the pseudo anti-resonance parameter determination module 210 determines a pseudo anti-resonance parameter corresponding to the restricted pseudo anti-resonant frequency (S2002).

In the control of the pseudo anti-resonance, the pseudo anti-resonant frequency as to the pseudo anti-resonance characteristics, the magnitude thereof, or the like is specified or changed such that, for example, the first-order pseudo anti-resonant frequency F1 and the second-order pseudo anti-resonant frequency F2 are specified or changed in a restricted existing range defined by the upper and lower limits. The pseudo anti-resonance parameter determination module 210 determines the pseudo anti-resonance parameter in the restricted range.

The acoustic signal receiving module 201 receives an acoustic signal to be a sound source used for reproduction (S2003).

The resonance characteristic compensator 220 performs compensation to reflect the pseudo anti-resonance in the acoustic signal using the pseudo anti-resonance parameter (S2004) After that, the output module 203 outputs the compensated acoustic signal (S2005).

Figure 14:
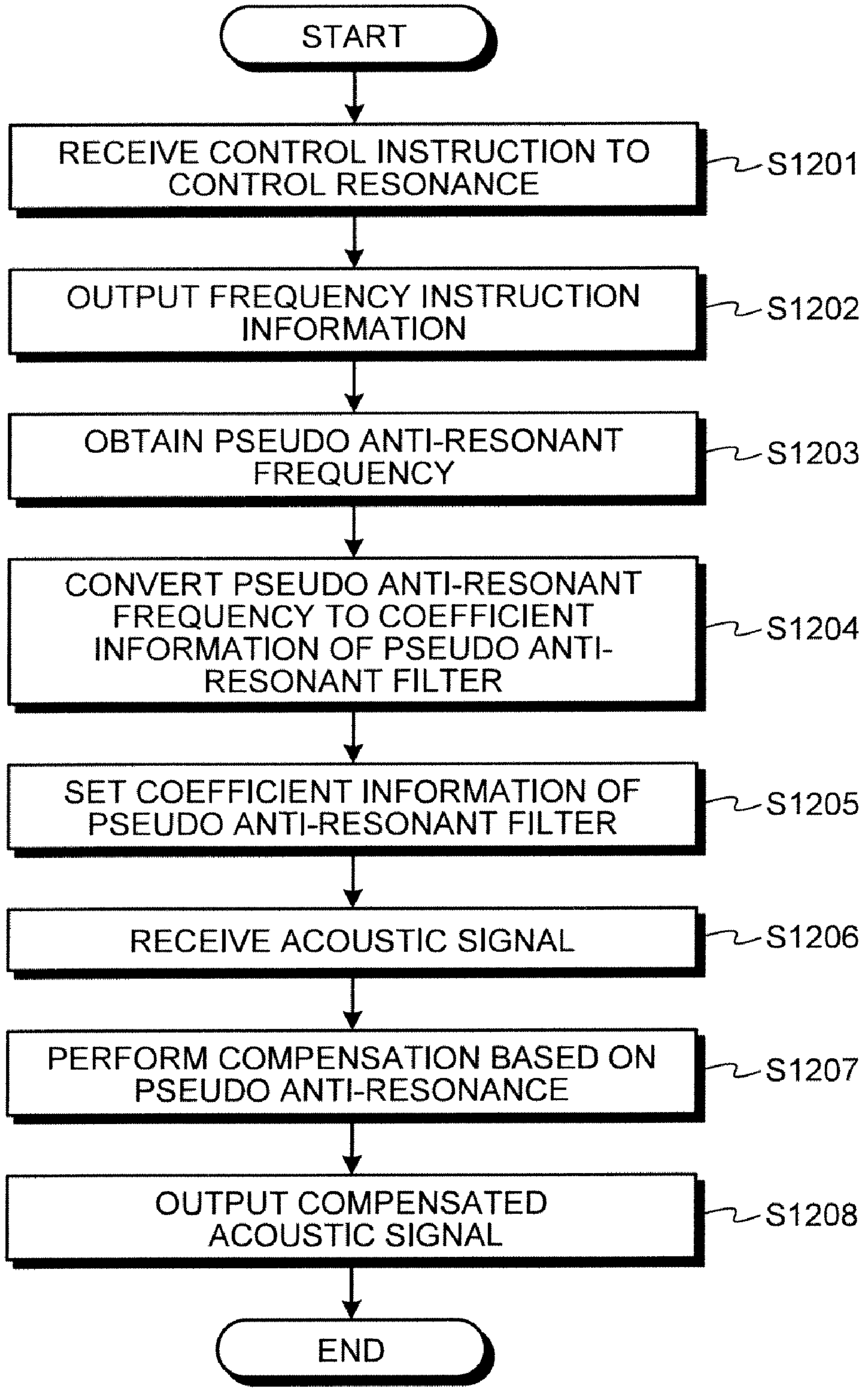
FIG. 14 is an exemplary detailed flowchart of the operation of the acoustic signal compensator in the first embodiment.

With reference to FIG. 14, the above operation of the acoustic signal compensator 150 will be described in detail.

First, the control receiver 205 receives a control instruction to control resonance characteristics such as information representing resonant frequencies and the magnitude relation between the frequencies to suppress the resonance (S1201). Input to the control receiver 205 is not limited to such a control instruction, and the control receiver 205 may receive a resonant frequency measured with earphones for resonance measurement.

The pseudo anti-resonance controller 204 outputs the frequency instruction information f indicating an input or measured resonant frequency to the pseudo anti-resonance parameter obtaining module 212 (S1202). The pseudo anti-resonant frequency obtaining module 215 outputs the frequency instruction information f to the pseudo anti-resonant frequency restriction module 211.

Next, according to the frequency instruction information f and the restriction conditions retained by the pseudo anti-resonant frequency restriction module 211, the pseudo anti-resonant frequency restriction module 211 gives a restriction or compensation instruction related to a pseudo anti-resonant frequency to be the center of suppression (for example, the first to Nth-order pseudo anti-resonant frequencies) to the pseudo anti-resonant frequency obtaining module 215. With this, the pseudo anti-resonant frequency obtaining module 215 obtains the pseudo anti-resonant frequency reflecting the restrictions (S1203). For example, the first-order pseudo anti-resonant frequency F1 and the second-order pseudo anti-resonant frequency F2 are obtained by compensating each of them to be within a restricted existing range determined in advance based on the restrictions related to the mutual relation therebetween.

The pseudo anti-resonant filter converter 214 of the pseudo anti-resonance parameter obtaining module 212 converts the received pseudo anti-resonant frequency (for example, the first to Nth-order pseudo anti-resonant frequencies) to coefficient information of a pseudo anti-resonant filter as an example of the pseudo anti-resonance parameter (S1204).

The pseudo anti-resonance controller 204 sets the coefficient information of the pseudo anti-resonant filter to the anti-resonance characteristic assignment module of the resonance characteristic compensator 220, e.g., the first to Nth-order anti-resonance characteristic assignment modules 221*a* to 221*n* (S1205).

After the coefficient information of the pseudo anti-resonant filter is set to the anti-resonance characteristic assignment module of the resonance characteristic compensator 220 (e.g., the first to Nth-order anti-resonance characteristic assignment modules 221*a* to 221*n*), the acoustic signal receiving module 201 receives an acoustic signal (S1206), Needless to say, the acoustic signal may be received at any stage before the setting.

The anti-resonance characteristic assignment module of the resonance characteristic compensator resonance characteristic compensator 220 (e.g., the first to Nth-order anti-resonance characteristic assignment modules 221*a* to 221*n*) compensates the acoustic signal based on the pseudo anti-resonant filter (S1207).

Then, the output module 203 outputs the acoustic signal compensated by the resonance characteristic compensator 220 to the earphone 120 (S1208).

While, in the first embodiment, coefficient information of pseudo anti-resonant filters are stored in the filter coefficient storage module 611 in advance and appropriate coefficient information is read therefrom based on the obtained pseudo anti-resonant frequency, it is not so limited. For example, the coefficient of the pseudo anti-resonant filter may be calculated from the frequency instruction information f based on the restriction conditions related to the pseudo anti-resonant frequency. In this case, based on the frequency instruction information F, a band-reject filter to suppress frequency characteristics in a frequency band corresponding to the frequency instruction information F is generated. With this, it is possible to reduce memory capacity required to store filter information. Incidentally, the band-reject filter can be designed by a known method, and the description will not be provided.

The resonant frequency instruction information used to obtain the pseudo anti-resonant frequency may be based on user operation as in the first embodiment, may be based on the result of actual measurement obtained by a microphone provided to earphones, or the like.

Although the first embodiment specifically describes the case where the first and second-order resonance peaks exist, three resonance peaks may exist. This applies similarly to the following embodiments and modifications thereof. For example, in the case of the third-order pseudo anti-resonant frequency F3, by using a frequency higher than the double of the first-order pseudo anti-resonant frequency F1 and lower than the triple thereof as the third-order pseudo anti-resonant frequency F3, an acoustic signal can be compensated to reflect pseudo anti-resonance characteristics corresponding to higher-order resonance. Also in the case of the Nth (more than three)-order pseudo anti-resonant frequency FN, by using a non-integral multiple of the first-order pseudo anti-resonant frequency F1 higher than a value obtained by multiplying the first-order resonant frequency F1 by (N−1) and lower than a value obtained by multiplying the first-order resonant frequency by N as the Nth-order pseudo anti-resonant frequency FN, an acoustic signal can be compensated to reflect pseudo anti-resonance characteristics corresponding to further higher-order resonance.

As described above, according to the first embodiment, the acoustic signal compensator 150 sets a restriction condition such that a pseudo anti-resonant frequency is higher than 5 kHz. Thus, the resonance peak of canal type earphones and the like can be appropriately suppressed. This can be seen from FIG. 6 indicating data obtained by measurement in the ears of various users, in which the first-order resonant frequencies f1 on the horizontal axis are distributed at frequencies of 5 kHz and higher.

According to the first embodiment, the acoustic signal compensator 150 prevents resonance before it occurs based on a plurality of orders of pseudo anti-resonant frequencies. Thus, ear resonance, which is not a single resonance, can be appropriately suppressed and compensated.

According to the first embodiment, the acoustic signal compensator 150 configured as above performs compensation based on the relation between respective orders of resonances (for example, between the first order and the second order, or between the first order and the Nth order). Thus, it is possible to reduce the feeling that the sound reproduced through earphones is closed.

The first embodiment is not limited to the above example, but may be capable of various modifications and alternative forms. An example of such modification will be described below.

According to a modification of the first embodiment, whether to perform compensation can be selected by the user. The acoustic signal compensator 150 of the modification is of basically the same configuration as that of the first embodiment, and therefore the description will not be repeated.

Figure 15:
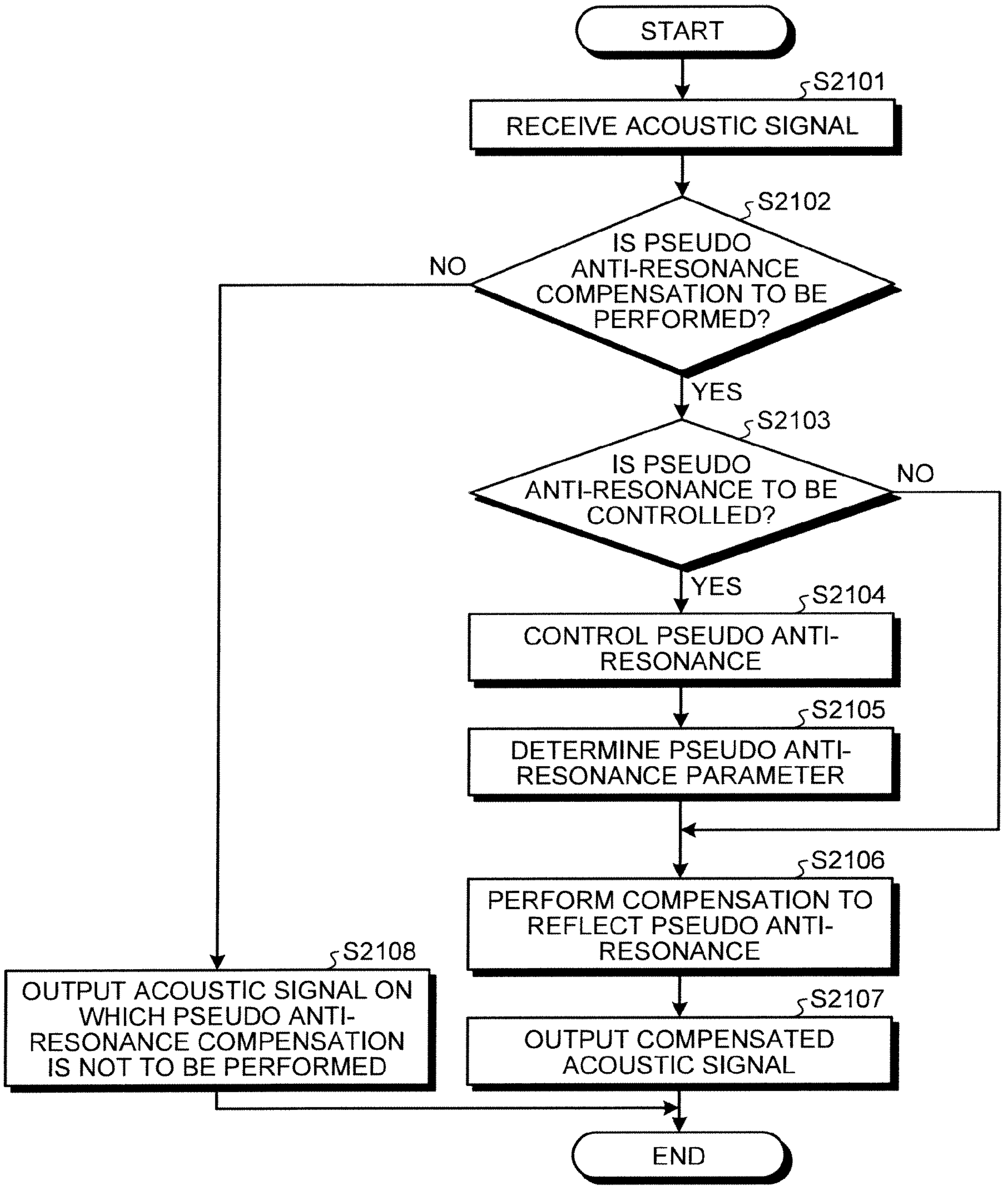
FIG. 15 is an exemplary flowchart of the operation of the acoustic signal compensator according to a modification of the first embodiment.

Described below is the operation of the acoustic signal compensator 150 to compensate an acoustic signal according to the modification. FIG. 15 is a flowchart of the operation of the acoustic signal compensator 150 to compensate an acoustic signal according to the modification.

The acoustic signal receiving module 201 receives an acoustic signal to be a sound source used for reproduction (S2101).

Then, a module in the acoustic signal compensator 150 (for example, the control receiver 205) selects whether to perform compensation by pseudo anti-resonance (S2102). If it is selected not to perform the compensation by pseudo anti-resonance (No at S2102), the output module 203 outputs an acoustic signal on which compensation is not to be performed by pseudo anti-resonance (S2108).

On the other hand, if it is selected to perform the compensation by pseudo anti-resonance (Yes at S2102), the module in the acoustic signal compensator 150 (for example, the control receiver 205) determines whether to control the pseudo anti-resonance if necessary (S2103). If it is determined not to control the pseudo anti-resonance (No at S2103), the acoustic signal is compensated using pseudo anti-resonance characteristics already set (S2106). The output module 203 outputs the compensated acoustic signal (S2107).

If it is determined to control the pseudo anti-resonance (Yes at S2103), the pseudo anti-resonance controller 204 control the pseudo anti-resonance in the pseudo anti-resonance parameter determination module 210 based on instruction information for pseudo anti-resonance characteristics received by the control receiver 205 (S2104).

Under the control of the pseudo anti-resonance controller 204, the pseudo anti-resonance parameter determination module 210 restricts a pseudo anti-resonant frequency to a restricted range according to the restrictions related to the pseudo anti-resonant frequency in response to the instruction information for the pseudo anti-resonance characteristics. Thus, the pseudo anti-resonance parameter determination module 210 determines a pseudo anti-resonance parameter corresponding to the restricted pseudo anti-resonant frequency (S2105).

The resonance characteristic compensator 220 performs compensation to reflect the pseudo anti-resonance in the acoustic signal using the pseudo anti-resonance parameter (S2106) After that, the output module 203 outputs the compensated acoustic signal (S2107).

Figure 16:
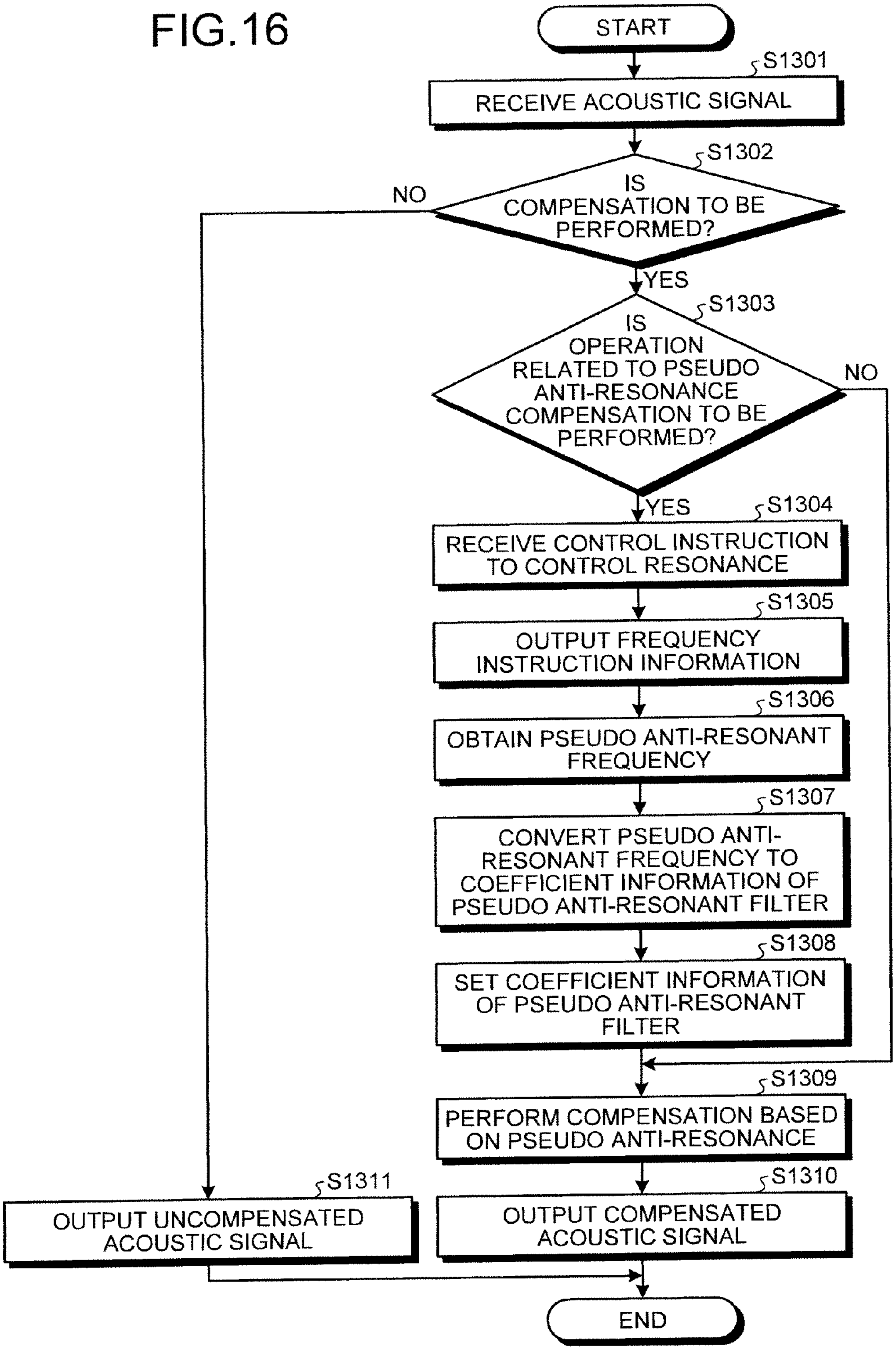
FIG. 16 is an exemplary detailed flowchart of the operation of the acoustic signal compensator in the modification.

With reference to FIG. 16, the above operation of the acoustic signal compensator 150 will be described in detail.

First, the acoustic signal receiving module 201 receives an acoustic signal (S1301).

After that, the control receiver 205 receives a selection as to whether to perform compensation (S1302). That is, the control receiver 205 functions as a selector to select whether to perform compensation by pseudo anti-resonance. If it is selected not to perform the compensation (No at S1302), the resonance characteristic compensator 220 does not compensate the acoustic signal and outputs the uncompensated acoustic signal (S1311).

On the other hand, if it is selected to perform the compensation (Yes at S1302), the control receiver 205 receives an input as to whether to perform operation related to compensation by pseudo anti-resonance (S1303). If the control receiver 205 receives an input not to perform the operation (No at S1303), the process moves to S1309. Coefficient information of a pseudo anti-resonant filter used for the compensation may be set in advance as default or may be set at the last time. In this manner, the control receiver 205 functions as an adjustment selector to select whether to adjust coefficient information of a pseudo anti-resonant filter.

If the control receiver 205 receives an input to perform the operation (Yes at S1303), the same process as S1201 to S1205 of FIG. 14 is performed, and the coefficient information of the is set (S1304 to 31308).

After that, the anti-resonance characteristic assignment module (for example, the first to Nth-order anti-resonance characteristic assignment modules 221*a* to 221*n*) of the resonance characteristic compensator 220 compensates the received acoustic signal based on the set pseudo anti-resonant filter (S1309). After that, the output module 203 outputs the acoustic signal compensated by the resonance characteristic compensator 220 to the earphone 120 (S1310).

As described above, according to the modification, generally, after compensation characteristics suitable for the user are set, there is no need to frequently control the compensation. This reduces the operational load on the user and thereby increases the convenience.

According to the modification, the acoustic signal compensator 150 allows the user to select whether to perform the compensation. That is, the user can actually listen to the sound and check the difference when compensating or not compensating the acoustic signal. This enables to select whether to perform the compensation depending on whether a device connected to the earphone terminal produces expected resonance. Thus, it is possible to flexibly handle different reproduction devices or players according to user's preference.

According to the modification, the acoustic signal compensator 150 effectively compensates high-order resonance characteristics. Thus, it is possible to generate high-quality acoustic signal with no feeling of ear-closing due to resonance.

According to the modification, the acoustic signal compensator 150 can variably reflect the Nth-order pseudo anti-resonance characteristics ($N \geqq 2$) corresponding to the resonance order and the existing range of frequencies of ear resonance that occurs in a space between an earphone and the ear of the user wearing the earphones. Thus, it is possible to provides compensations suitable for different users, respectively. Moreover, since the frequency range of resonant frequencies and the mutual relation between high-order resonant frequencies can be used, it is possible to provide sound compensation in which ear resonance is effectively compensated in the minimum variable range.

A second embodiment will be described below. While the first embodiment describes an example in which the pseudo anti-resonance controller 204 outputs the frequency instruction information f, the output parameter is not limited to the frequency instruction information f. The output parameter may be a sensory instruction based on user's operation.

Figure 17:
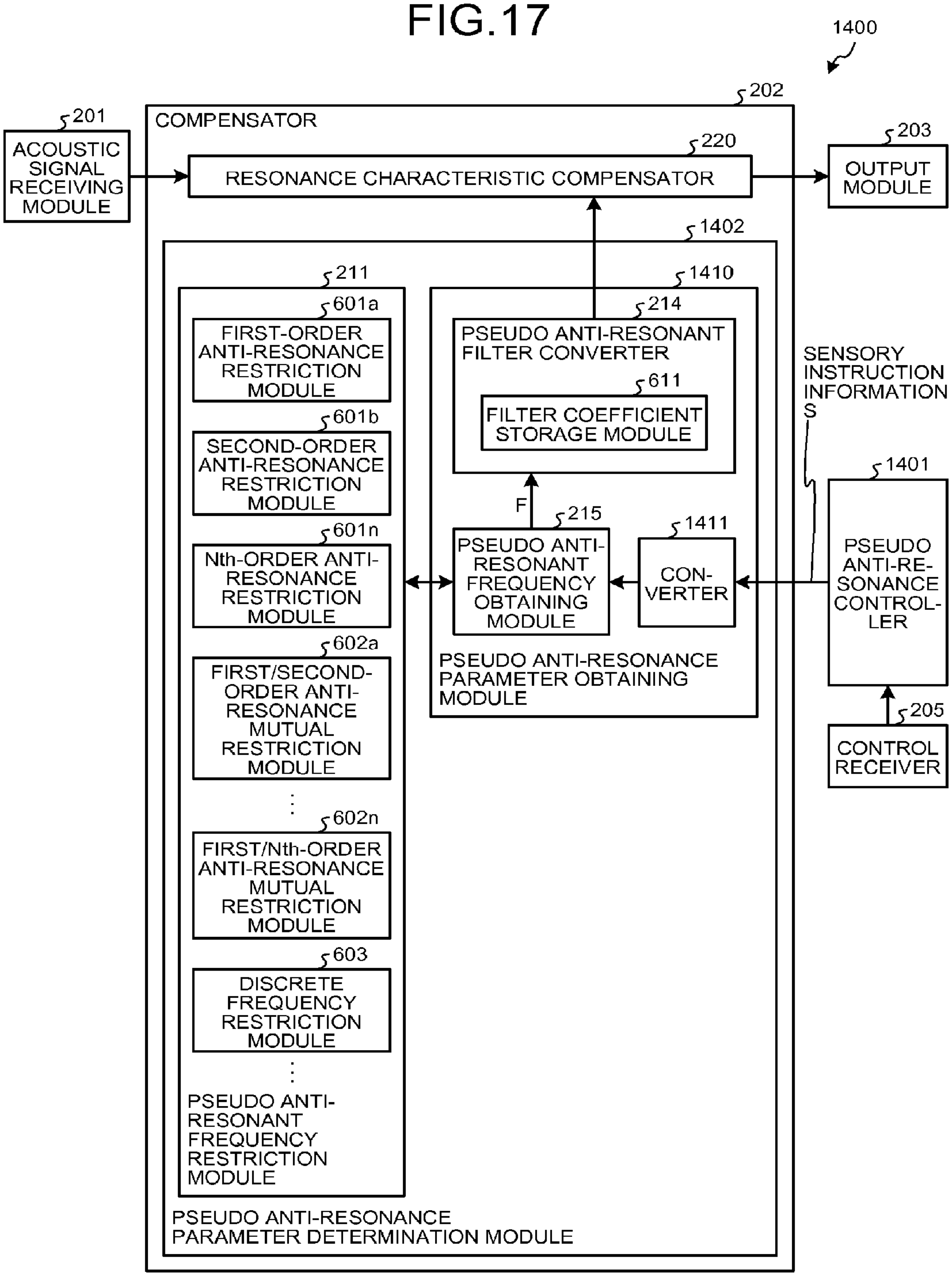
FIG. 17 is an exemplary block diagram of a pseudo anti-resonance parameter determination module and a pseudo anti-resonance controller according to a second embodiment.

FIG. 17 is a block diagram of an acoustic signal compensator 1400 comparing a pseudo anti-resonance parameter determination module 1402 and a pseudo anti-resonance controller 1401 according to the second embodiment. Otherwise, the acoustic signal compensator 1400 is of basically the same configuration as the acoustic signal compensator 150 of the first embodiment, and the description will not be repeated. In the second embodiment, after calculating coefficient information of a pseudo anti-resonant filter based on sensory instruction information S received from the pseudo anti-resonance controller 1401, the pseudo anti-resonance parameter determination module 1402 sets the coefficient information.

In the second embodiment, upon receipt of sensory instruction information from the user through the control receiver 205, sound compensation is performed based on the sensory instruction information. The sensory instruction information indicates an instruction related to compensation based on user's feeling or sense received as a selection of one of a plurality of discrete or sequential levels set in advance based on user's operation.

Examples of the sensory instruction information includes information indicating an instruction from the user to increase or decrease a pseudo anti-resonant frequency for resonance compensation, information indicating an instruction to change the level of a pseudo anti-resonant frequency for resonance compensation, and the like. Such a selection of a level may be provided through various user interfaces (UIs) installed on the acoustic signal compensator 1400. For example, a selection may be made with a key or a button, or through a graphical user interface (GUI) using the display module of the sound player 110. At that time, the display module may displays a result of sensing video, audio, and other information to receive a selection of a level related to compensation.

The pseudo anti-resonance parameter determination module 1402 comprises the pseudo anti-resonant frequency restriction module 211 and a pseudo anti-resonance parameter obtaining module 1410. The pseudo anti-resonance parameter obtaining module 1410 comprises the pseudo anti-resonant filter converter 214, the pseudo anti-resonant frequency obtaining module 215, and a convertor 1411. Constituent elements corresponding to those of the first embodiment is designated by like reference numerals, and their description will not be repeated.

The convertor 1411 converts the sensory instruction information S received from the pseudo anti-resonance controller 1401 to the frequency instruction information f. Thereafter, the process is performed in the same manner as previously described in the first embodiment, and therefore the description will not be repeated.

Figure 18:
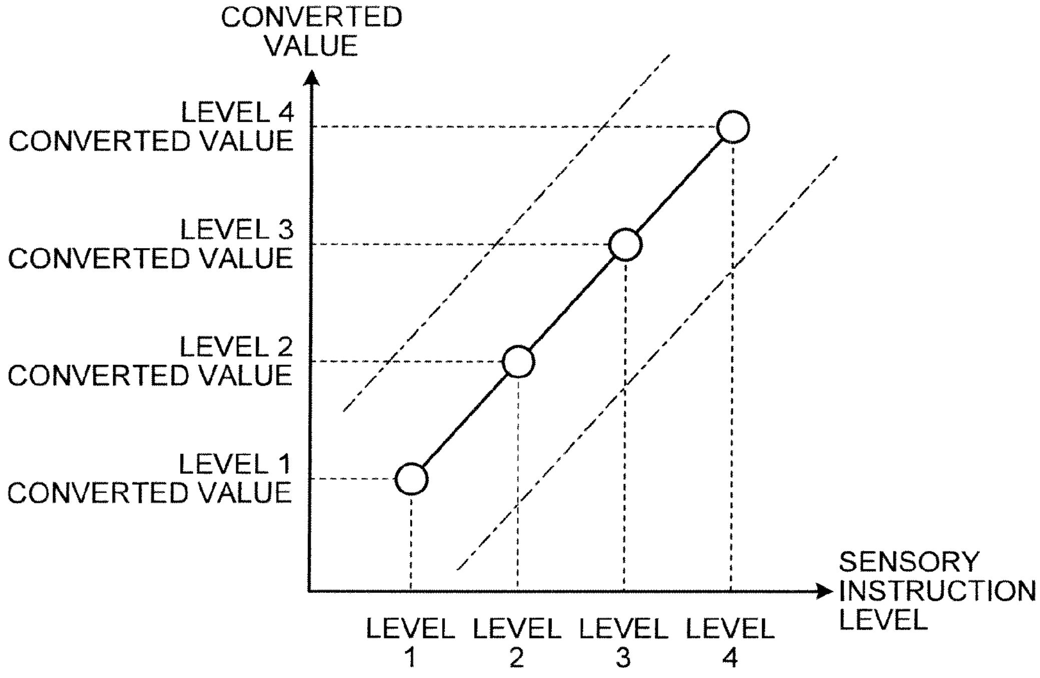
FIGS. 18 and 19 are exemplary charts of the relation between sensory instruction information S and frequency instruction information f converted from the sensory instruction information S in the second embodiment.
Figure 19:
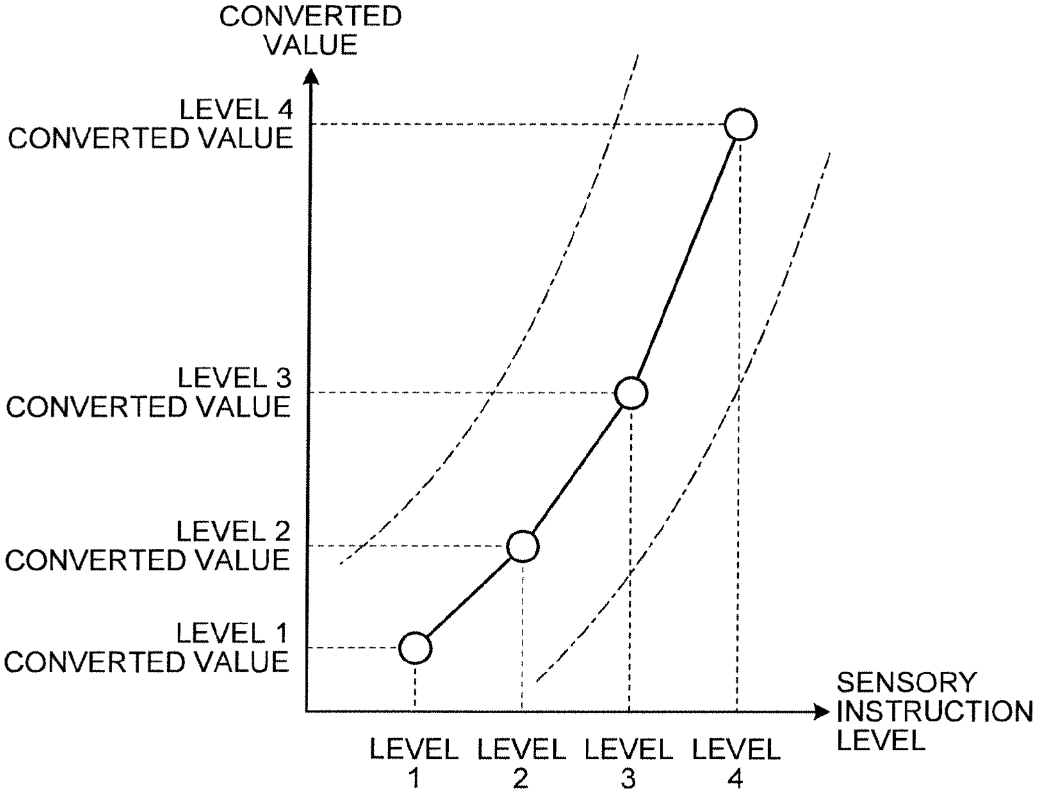

With reference to FIGS. 18 and 19, a description will be given of conversion performed by the convertor 1411. FIG. 18 illustrates an example of the relation between the sensory instruction information S and the frequency instruction information f converted from the sensory instruction information S.

In the example of FIG. 18, sensory instruction levels represented by the horizontal axis and converted values (for example, sizes of frequencies) at the respective levels are set at about equal intervals and are in an almost linear relation. The sensory instruction information S may be converted to the frequency instruction information f based on such a linear relation.

In the example of FIG. 19, while the sensory instruction levels represented by the horizontal axis are set at about equal intervals, converted values (for example, sizes of frequencies) at the respective levels are set at exponential intervals on the linear axis (at about equal intervals on the logarithmic axis). That is, depending on a sensory instruction level specified by the user, resonant frequencies are selected at exponential intervals. This is because the human auditory sense recognizes a frequency increase in an exponential manner as a linear increase. Thus, a frequency can be selected according to the intuitive sense of the user.

Otherwise, the second embodiment is basically similar to the first embodiment, and the description will not be repeated. As described above, according to the second embodiment, the acoustic signal compensator 1400 enables pseudo anti-resonance characteristics to be selected or adjusted according to user's preference in addition to the effect achieved by the acoustic signal compensator 150.

The embodiments are not limited to the above example, but may be capable of various modifications and alternative forms. An example of such modification will be described below.

In the first and the second embodiments, the resonance characteristic compensator 220 of the acoustic signal compensator comprises a different resonance characteristic compensator with respect to each order and compensation is performed using a different filter. However, it is not so limited. According to a first modification of the embodiments, a single resonance characteristic compensator performs compensation to reflect a plurality of orders of pseudo anti-resonance characteristics.

Figure 20:
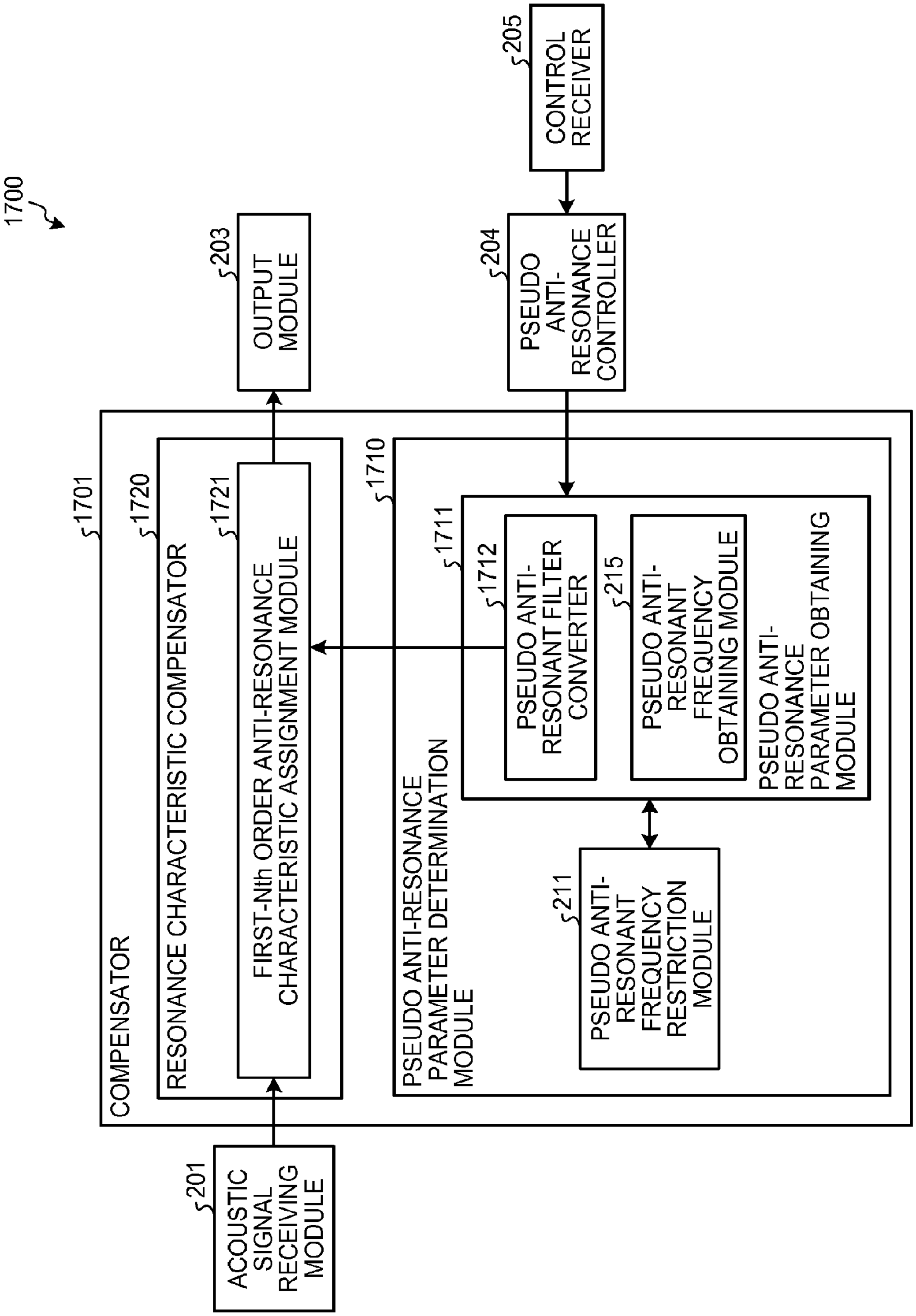
FIG. 20 is an exemplary block diagram of an acoustic signal compensator according to a first modification of the embodiments.

FIG. 20 is a block diagram of an acoustic signal compensator 1700 according to the first modification. As illustrated in FIG. 20, the acoustic signal compensator 1700 comprises a compensator 1701 different from the compensator 202 of the first embodiment. The compensator 1701 comprises a pseudo anti-resonance parameter determination module 1710 and a resonance characteristic compensator 1720.

The pseudo anti-resonance parameter determination module 1710 comprises a pseudo anti-resonance parameter obtaining module 1711 provided with a pseudo anti-resonant filter converter 1712. After performing conversion in the same manner as in the first embodiment, the pseudo anti-resonant filter converter 1712 sets coefficient information of the first to Nth-order pseudo anti-resonant filters to a first-Nth order anti-resonance characteristic assignment module 1721. In this manner, with the first-Nth order anti-resonance characteristic assignment module 1721 formed of a combination of all the first to Nth-order pseudo anti-resonant filters, the same compensation as that of the above embodiments can be performed.

As described above, according to the first modification, a single filter has a plurality of orders of pseudo anti-resonance characteristics. With this, a filter can be configured with less filter coefficients (less number of taps). Thus, it is possible to reduce the processing amount to compensate an acoustic signal and also reduce memory capacity required to store filter coefficients.

According to a second modification of the embodiments, two anti-resonance characteristic assignment modules perform compensation to reflect a plurality of orders of pseudo anti-resonance characteristics.

Figure 21:
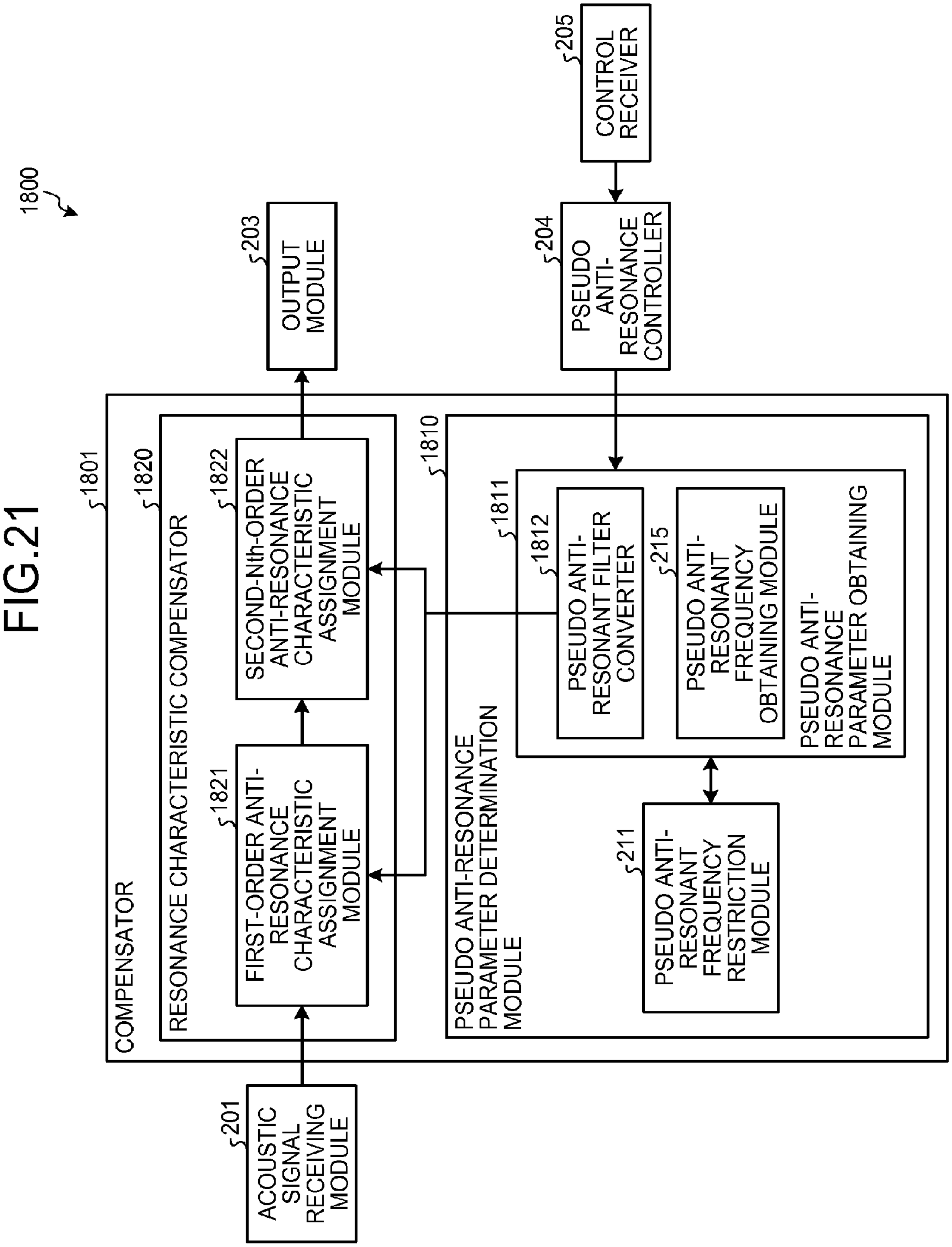
FIG. 21 is an exemplary block diagram of an acoustic signal compensator according to a second modification of the embodiments.

FIG. 21 is a block diagram of an acoustic signal compensator 1800 according to the second modification. As illustrated in FIG. 21, the acoustic signal compensator 1800 comprises a compensator 1801. The compensator 1801 comprises a pseudo anti-resonance parameter determination module 1810 and a resonance characteristic compensator 1820.

The pseudo anti-resonance parameter determination module 1810 comprises a pseudo anti-resonance parameter obtaining module 1811 provided with a pseudo anti-resonant filter converter 1812. Apart from performing conversion in the same manner as in the first and the second embodiments, the pseudo anti-resonant filter converter 1812 sets coefficient information of the first-order pseudo anti-resonant filter to a first-order anti-resonance characteristic assignment module 1821. Further, the pseudo anti-resonant filter converter 1812 sets coefficient information of the second to Nth-order pseudo anti-resonant filters to a second-Nth-order anti-resonance characteristic assignment module 1822. In this manner, with the two anti-resonance characteristic assignment modules, the same compensation as that of the above embodiments can be performed.

In this case, for the first-order anti-resonance characteristics, a filter independent of the second and higher-order anti-resonance characteristics can be used. Accordingly, the acoustic signal compensator 1800 of the second modification is capable of controlling a combination of a filter representing the first-order anti-resonance characteristics and a filter representing the second-order and higher anti-resonance characteristics.

With this configuration, after determining the first-order main pseudo anti-resonance characteristics (for example, the frequency F1 related to the first-order anti-resonance characteristics), the acoustic signal compensator 1800 of the second modification can determine or narrow down pseudo anti-resonant frequencies F2, . . . , and Fn based on restrictions related to the mutual relation between the first-order resonant frequency and the higher-order resonant frequency (for example, $Fm=\alpha m*F1$, $\alpha m<m$ ($m=2, \ldots, N$)). Thus, the acoustic signal compensator 1800 can effectively determine or select a filter having the derived second to Nth-order anti-resonance characteristics.

Regarding the second to Nth-order anti-resonance characteristics, a single filter has a plurality of high orders of anti-resonance characteristics. With this, a filter can be configured with less filter coefficients (less number of taps). Thus, it is possible to reduce the processing amount to compensate an acoustic signal and also reduce memory capacity required to store filter coefficients.

The various modules of the systems described herein can be implemented as software applications, hardware and/or software modules, or components on one or more computers, such as servers. While the various modules are illustrated separately, they may share some or all of the same underlying logic or code.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A sound signal compensator comprising:

a sound signal receiving module configured to receive a sound signal;

a compensator configured, as compensation of acoustic characteristics of a plurality of orders of resonances when an earphone or a headphone is worn, to suppress a first frequency amplitude as compensation of a first-order resonance of the resonances and to suppress a second frequency amplitude as compensation of a higher-order resonance than the first-order resonance, wherein the second frequency is higher than the first frequency and is lower than twice the first frequency; and an output module configured to output the sound signal compensated by the compensator.

2. The sound signal compensator of claim 1, wherein a ratio (F2/F1) of the second frequency F2 to the first frequency F1 reduces as the first frequency is higher.

3. The sound signal compensator of claim 1, wherein the first frequency and the second frequency are higher than 5 kHz.

4. The sound signal compensator of claim 1, further comprising a selector configured to select whether to perform the compensation by the compensator.

5. A sound signal compensator comprising:

a sound signal receiving module configured to receive a sound signal;

a compensator configured, as compensation of acoustic characteristics of a plurality of orders of resonances when an earphone or a headphone is worn, to suppress a first frequency amplitude as compensation of a first-order resonance of the resonances and to suppress a second frequency amplitude as compensation of an Nth-order resonance higher than the first-order resonance, wherein the second frequency is lower than N times the first frequency and is higher than (N−1) times the first frequency, and N is an integer 2 or more; and an output module configured to output the sound signal compensated by the compensator.

6. The sound signal compensator of claim 5, wherein a ratio (F2/F1) of the second frequency F2 to the first frequency F1 reduces as the first frequency is higher.

7. The sound signal compensator of claim 5, further comprising a selector configured to select whether to perform the compensation by the compensator.

8. A sound signal compensation method applied to a sound signal compensator, comprising:

receiving a sound signal;

suppressing, as compensation of acoustic characteristics of a plurality of orders of resonances when an earphone or a headphone is worn, a first frequency amplitude as compensation of a first-order resonance of the resonances and suppressing a second frequency amplitude as compensation of a higher-order resonance than the first-order resonance, wherein the second frequency is higher than the first frequency and is lower than twice the first frequency; and outputting the sound signal compensated by the compensation.

9. The sound signal compensator of claim 8, wherein a ratio (F2/F1) of the second frequency F2 to the first frequency F1 reduces as the first frequency is higher.

10. The sound signal compensator of claim 8, wherein the first frequency and the second frequency are higher than 5 kHz.

11. The sound signal compensator of claim 8, further comprising selecting whether to perform the compensation by the compensator.

* * * * *